United States Patent
Chiang et al.

(10) Patent No.: US 6,451,319 B1
(45) Date of Patent: Sep. 17, 2002

(54) RECOMBINANT AND MUTANT ADENOVIRUSES

(75) Inventors: Christina H. Chiang, San Diego; Mark D. Cochran, Carlsbad, both of CA (US)

(73) Assignee: Schering-Plough Veterinary Corporation, Kenilworth, NJ (US)

( * ) Notice: Subject to any disclaimer, the term of this patent is extended or adjusted under 35 U.S.C. 154(b) by 0 days.

(21) Appl. No.: 09/545,481

(22) Filed: Apr. 7, 2000

Related U.S. Application Data

(60) Provisional application No. 60/128,766, filed on Apr. 9, 1999.

(51) Int. Cl.$^7$ .............................................. A61K 39/12
(52) U.S. Cl. ................................ 424/199.1; 424/205.1; 424/233.1; 435/69.1; 435/235.1; 435/320.1
(58) Field of Search ........................... 424/199.1, 205.1, 424/233.1; 435/69.1, 235.1, 320.1; 935/32, 57, 65

(56) References Cited

U.S. PATENT DOCUMENTS

| | | | |
|---|---|---|---|
| 4,510,245 A | 4/1985 | Cousens et al. | 435/172.3 |
| 4,920,209 A | 4/1990 | Davis et al. | 435/235 |
| 5,151,267 A | 9/1992 | Babiuk et al. | 424/87 |
| 5,399,346 A | 3/1995 | Anderson et al. | 424/932.1 |
| 5,820,868 A | 10/1998 | Mittal et al. | |
| 6,001,591 A | 12/1999 | Mittal et al. | |
| 6,086,890 A | 7/2000 | Mittal et al. | |

FOREIGN PATENT DOCUMENTS

| | | |
|---|---|---|
| EP | 0389286 | 9/1990 |
| EP | 0259149 B1 | 12/1993 |
| WO | WO 91/11525 | 8/1991 |
| WO | WO 96/12030 | 4/1996 |
| WO | WO 98/00166 | 1/1998 |

OTHER PUBLICATIONS

Brough et al. A gene transfer vector cell line system for complete functional complementation of adenovirus early regions E1 and E4. Journal of Virology (1996) vol. 70, No. 9, pp. 6497–6501.*

Altschul, S.F. et al. (1997) Gapped Blast and PSI–Blast, a new generations of protein database search programs. Nucl. Acid. Res., vol. 25, pp. 3389–3402.

Baxi, M.K. et al. (1999) Transcription map and expression of bovine herpesvirus–1 glucoprotein D in early region 4 of bovine adenovirus–3. Virology, vol. 261, pp. 143–152.

Benko, M. et al. (1988) DNA restriction enzyme analysis of bovine adenoviruses. Intervirology, vol. 29, pp. 346–350.

Benko, M. et al. (1990) Restriction site mapping of bovine adenovirus type 1. Acta Vet. Hungarica, vol. 38, pp. 281–284.

Chartier, C. et al. (1996) Efficient generation of recombinant adenovirus vectors by homologous recombinaation in Escherichia coli. J. of Virol., vol. 70, pp. 4805–4810.

Collett, M.S. et al. (1988) Proteins encoded by bovine viral diarrhea virus: The genomic organization of a pestivirus. Virology, vol. 165, pp. 200–208.

Evans, P.S. et al. (1998) Sequence, transcriptional analysis and deletion of the bovine adenovirus type 1 E3 region. Virology, vol. 244, pp. 173–185.

Fenner, F. et al. (1987) Mechanisms of disease production: Acute infections. Veterinary Virology, Academic Press, Inc., pp. 183–202.

Hanahan, D. et al. (1983) Studies on transformation of Escherichia coli with plasmids. J. Mol. Biol., vol. 166, pp. 557–580.

Hammond, J.M. et al. (2000) Vaccination with a single dose of a recombinant porcine adenovirus expressing the classical swine fever virus gp55 (E2) gene protects pigs against classical swine fever. Vaccine, vol. 18, pp. 1040–1050.

He, T–C et al. (1998) A simplified system for generating recombinant adenoviruses. P.N.A.S USA, vol. 95, pp. 2509–2514.

Hjerpe, C.A. (1986) The bovine respiratory disease complex. Current Veterinary Therapy 2: Food Amimal Practice, Ed. J.L. Howard, Pub W.B. Saunders Co. pp. 670–681.

Jackwood, M.W. (1999) Current and future recombinant viral vaccine for poultry. Advances in Veterinary Medicine, Veterinary Vaccines and Diagnostics, vol. 41, Ed. R.D. Schultz, Academic Press Inc. pp. 517–522.

Katz, J.M. et al. (1990) Direct sequencing of the HA gene of influenza (H3N2) virus in original clinical samples reveals sequence identity with mammalian cell–grown virus. J. of Virol., vol. 64, pp. 1808–1811.

Lathe, R. et al. (1987) Plasmid and bacteriophage vectors for excision of intact inserts. Gene, vol. 57, pp. 193–201.

Laemmli, U.K. (1970) Cleavage of structural proteins during the assembly of the head of bacteriophage T4. Nature, vol. 227, pp. 680–685.

Reddy, P.S. et al. (1999) Development of porcine adenovirus–3 as an expression vector. J. of Gen. Virol., vol. 80, pp. 563–570.

(List continued on next page.)

Primary Examiner—Jeffrey Stucker
Assistant Examiner—Ulrike Winkler

(57) ABSTRACT

The present invention provides novel viral vectors. In one embodiment, the present invention provides mutant and recombinant bovine adenoviruses having a deletion and/or insertion of DNA in the early gene region 4 (E4). In another embodiment, the present invention provides mutant and recombinant bovine adenovirus 1 viruses having a deletion and/or insertion of DNA in the early gene region 3 (E3). The present invention also contemplates the use of the viral vectors for vaccination, gene therapy or other applications as suitable.

7 Claims, 1 Drawing Sheet

OTHER PUBLICATIONS

Figure 1:
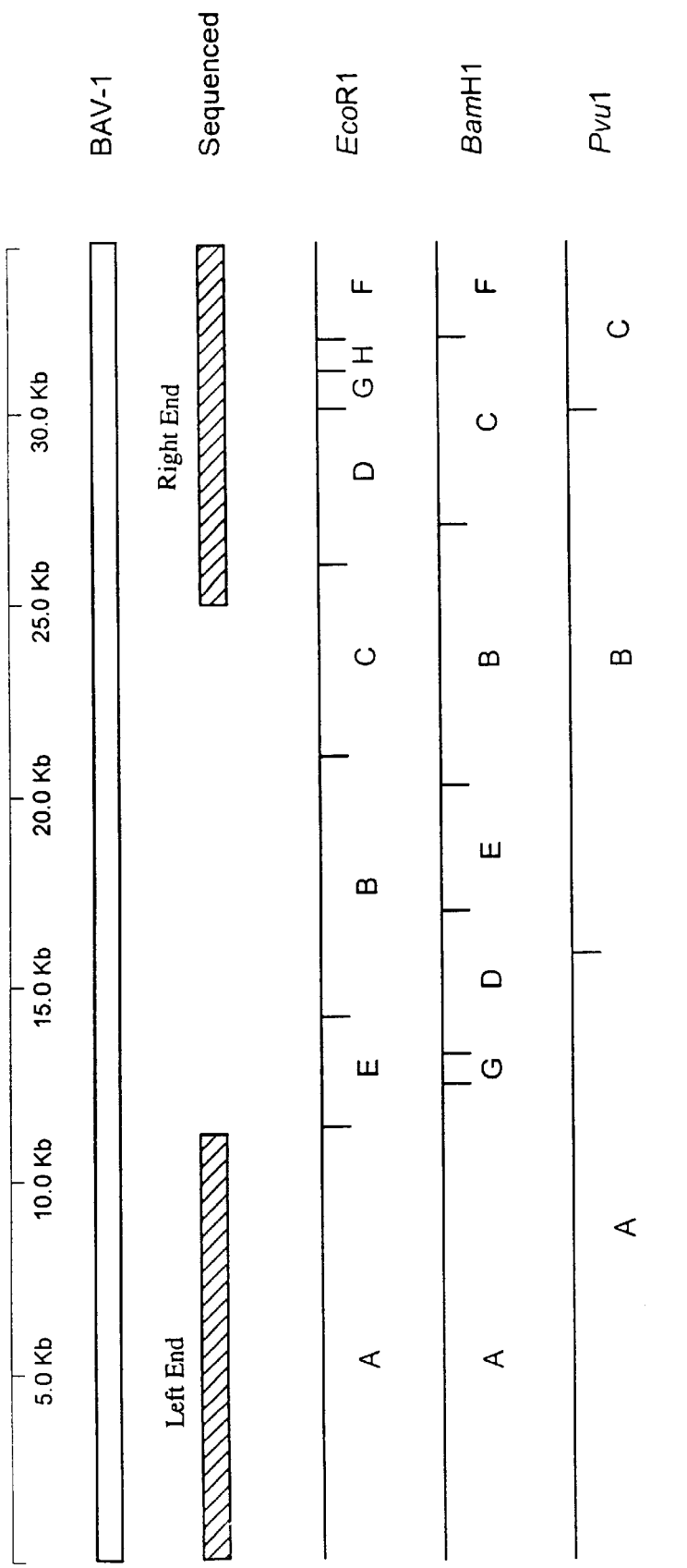

Reddy, P.S. et al. (1999) Replication–defective adenovirus type 3 as an expression vector. J. of Virol., vol. 73, pp. 9137–9144.

Scharf, S.J. (1990) Cloning with PCR. *PCR Protocols: A Guide to Methods and Applications*, Academic Press Inc., pp. 84–91.

Sharma, J.M. (1999) Introduction to poultry vaccines and immunity. *Advances in Veterinary Medicine, Veterinary Vaccines and Diagnostics*, vol. 41, Ed. R.D. Schultz, Academic Press Inc. pp. 517–522.

Sheppard, M. (1999) Viral vectors for veterinary vaccines. *Advances in Veterinary Medicine, Veterinary Vaccines and Diagnostics*, vol. 41, Ed. R.D. Schultz, Academic Press Inc. pp. 145–161.

\* cited by examiner

RECOMBINANT AND MUTANT ADENOVIRUSES

The benefit of the Apr. 9, 1999 filing date of Provisional Application No. 60/128,766 is claimed.

FIELD OF THE INVENTION

The present invention relates to viral vectors for vaccination of animals. In particular, the present invention pertains to viral vectors having insertion sites for the introduction of foreign DNA.

BACKGROUND OF THE INVENTION

The adenoviruses cause enteric or respiratory infection in humans as well as in domestic and laboratory animals.

Inserting genes into adenoviruses has been accomplished. In the human adenovirus (HuAd) genome there are two important regions: E1 and E3 in which foreign genes can be inserted to generate recombinant adenoviruses.

This application of genetic engineering has resulted in several attempts to prepare adenovirus expression systems for obtaining vaccines. Examples of such research include the disclosure of U.S. Pat. No. 4,510,245 of an adenovirus major late promoter for expression in a yeast host; U.S. Pat. No. 4,920,209 of a live recombinant adenovirus type 7 with a gene coding for hepatitis-B surface antigen; European patent No. 389,286 of a non-defective human adenovirus 5 recombinant expression system in human cells; and published International application No. WO 91/11525 of live non-pathogenic immunogenic viable canine adenovirus in a cell.

However, because they are more suitable for entering a host cell, an indigenous adenovirus vector would be better suited for use as a live recombinant virus vaccine in different animal species compared to an adenovirus of human origin. For example, bovine adenovirus-based expression vectors have been reported for bovine adenovirus 3 (BAV-3) (see U.S. Pat. No. 5,820,868).

Bovine adenoviruses (BAVs) comprise at least nine serotypes divided into two subgroups. These subgroups have been characterized based on enzyme-linked immunoassays (ELISA), serologic studies with immunofluorescence assays, virus-neutralization tests, immunoelectron microscopy and by their host specificity and clinical syndromes. Subgroup 1 viruses include BAV 1, 2, 3 and 9 and grow relatively well in established bovine cells compared to subgroup 2 viruses which include BAV 4, 5, 6, 7 and 8.

BAV-3 was first isolated in 1965 and is the best characterized of the BAV genotypes and contains a genome of approximately 35 kilobases. The locations of hexon and proteinase genes in the BAV-3 genome have been identified and sequenced.

Genes of the bovine adenovirus 1 (BAV-1) genome have also been identified and sequenced. However, the location and sequences of other genes such as certain early gene regions in the BAV genome have not been reported.

The continued identification of suitable viruses and gene insertion sites are valuable for the development of new vaccines. The selection of (i) a suitable virus and (ii) the particular portion of the genome to use as an insertion site for creating a vector for foreign gene expression, however, pose a significant challenge. In particular, the insertion site must be non-essential for the viable replication of the virus, as well as its operation in tissue culture and in vivo. Moreover, the insertion site must be capable of accepting new genetic material, while ensuring that the virus continues to replicate.

What is needed is the identification of novel viruses and gene insertion sites for the creation of new viral vectors.

SUMMARY OF THE INVENTION

In one embodiment, the present invention provides recombinant viruses. While not limited to a particular use, these recombinant viruses can be used to generate vaccines.

While not limited to a particular virus, in one embodiment the present invention provides a recombinant virus comprising a foreign DNA sequence inserted into the E4 gene region of a bovine adenovirus. In a preferred embodiment, the insertion is to a non-essential site. In another embodiment, the present invention provides a recombinant virus comprising a foreign DNA sequence inserted into the E3 gene region of a bovine adenovirus 1. In a preferred embodiment, the insertion is to a non-essential site.

While not limited to its ability to replicate, in a preferred embodiment, the recombinant virus is replication competent. Likewise, while not limited to the foreign DNA to be inserted, in a preferred embodiment, the foreign DNA encodes a polypeptide and is from a virus or bacteria selected from the group consisting of bovine rotavirus, bovine coronavirus, bovine herpes virus type 1, bovine respiratory syncytial virus, bovine para influenza virus type 3 (BPI-3), bovine diarrhea virus, bovine rhinotracheitis virus, bovine parainfluenza type 3 virus, *Pasteurella haemolytica, Pasteurella multocida* and/or *Haemophilus somnus*. In another preferred embodiment, the foreign DNA encodes a cytokine. In a further preferred embodiment, the polypeptide comprises more than ten amino acids and is antigenic. Finally, in a particularly preferred embodiment, the foreign DNA sequence is under the control of a promoter located upstream of the foreign DNA sequence.

The present invention also contemplates mutant viruses. While not limited to a particular mutant virus, in one embodiment, the mutant virus comprises a deletion of at least a portion of the E4 gene region of a bovine adenovirus. In a preferred embodiment, the deletion is of a non-essential site. In another embodiment, the virus comprises a deletion of at least a portion of the E3 gene region of a bovine adenovirus 1. In a preferred embodiment, the mutant virus is replication competent. In a further preferred embodiment, at least one open reading frame of the relevant gene region of the bovine adenovirus is completely deleted.

In yet another embodiment, the present invention provides a method for preparing a recombinant virus comprising inserting at least one foreign gene or gene fragment that encodes at least one antigen into the genome of a virus wherein said gene or gene fragment has been inserted into the early gene region 4 of a bovine adenovirus or inserted into the early gene region 3 of bovine adenovirus 1. In a preferred embodiment, the method includes the insertion of at least a part of the genome of a virus into a bacterial plasmid, transforming said bacteria with said plasmid, and incubating said bacteria at approximately 25° C.

In another embodiment, the present invention provides vaccines. While not limited to a particular vaccine, in one embodiment, the vaccines comprise the recombinant viruses described above.

The present invention also contemplates methods of vaccination, including, but not limited to, the introduction of the above-described vaccines to an animal.

Definitions The term, "animal" refers to organisms in the animal kingdom. Thus, this term includes humans, as well as other organisms. Preferably, the term refers to vertebrates. More preferably, the term refers to bovine animals.

A "vector" is a replicon, such as a plasmid, phage, cosmid or virus, to which another DNA sequence may be attached so as to bring about the expression of the attached DNA sequence.

For purposes of this invention, a "host cell" is a cell used to propagate a vector and its insert. Infecting the cell can be accomplished by methods well known to those skilled in the art, for example, as set forth in Transfection of BAV-1 DNA below.

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, viral DNA, and even synthetic DNA sequences. A polyadenylation signal and transcription termination sequence can be located 3' to the coding sequence.

A "promoter sequence" is a DNA regulatory region capable of binding RNA polymerase or an auxiliary protein and initiating transcription of a downstream (3' direction) coding sequence. For purposes of defining the present invention, the promoter sequence is in close proximity to the 5' terminus by the translation start codon (ATG) of a coding sequence and extends upstream (5' direction) to include the minimum number of bases or elements necessary to facilitate transcription at levels detectable above background. Within the promoter sequence will be found a transcription initiation site, as well as protein binding domains (consensus sequences) responsible for the binding of RNA polymerase. Eucaryotic promoters will often, but not always, contain "TATA" boxes and "CAAT" boxes, conserved sequences found in the promoter region of many eucaryotic organisms.

A coding sequence is "operably linked to" or "under the control of" promoter or control sequences in a cell when RNA polymerase will interact with the promoter sequence directly or indirectly and result in transcription of the coding sequence into mRNA, which is then translated into the polypeptide encoded by the coding sequence.

A "double-stranded DNA molecule" refers to the polymeric form of deoxyribonucleotides (adenine, guanine, thymine, or cytosine) in its normal, double-stranded helix. This term refers only to the primary and secondary structure of the molecule, and does not limit it to any particular tertiary forms. Thus, this term includes, for example, double-stranded DNA found in linear DNA molecules (e.g., restriction fragments of DNA from viruses, plasmids, and chromosomes), as well as circular and concatamerized forms of DNA.

A "foreign DNA sequence" is a segment of DNA that has been or will be attached to another DNA molecule using recombinant techniques wherein that particular DNA segment is not found in association with the other DNA molecule in nature. The source of such foreign DNA may or may not be from a separate organism than that into which it is placed. The foreign DNA may also be a synthetic sequence having codons different from the native gene. Examples of recombinant techniques include, but are not limited to, the use of restriction enzymes and ligases to splice DNA.

An "insertion site" is a restriction site in a DNA molecule into which foreign DNA can be inserted.

For purposes of this invention, a "homology vector" is a plasmid constructed to insert foreign DNA sequence in a specific site on the genome of an adenovirus.

The term "open reading frame" or "ORF" is defined as a genetic coding region for a particular gene that, when expressed, can produce a complete and specific polypeptide chain protein.

A cell has been "transformed" with exogenous DNA when such exogenous DNA has been introduced inside the cell membrane. Exogenous DNA may or may not be integrated (covalently linked) to chromosomal DNA making up the genome of the cell. In procaryotes and yeasts, for example, the exogenous DNA may be maintained on an episomal element, such as a plasmid. A stably transformed cell is one in which the exogenous DNA has become integrated into the chromosome so that it is inherited by daughter cells through chromosome replication. For mammalian cells, this stability is demonstrated by the ability of the cell to establish cell lines or clones comprised of a population of daughter cells containing the exogenous DNA.

A "replication competent virus" is a virus whose genetic material contains all of the DNA or RNA sequences necessary for viral replication as are found in a wild-type of the organism. Thus, a replication competent virus does not require a second virus or a cell line to supply something defective in or missing from the virus in order to replicate. A "non-essential site in the adenovirus genome" means a region in the adenovirus genome, the polypeptide product or regulatroy sequence of which is not necessary for viral infection or replication.

Two polypeptide sequences are "substantially homologous" when at least about 80% (preferably at least about 90%, and most preferably at least about 95%) of the amino acids match over a defined length of the molecule.

Two DNA sequences are "substantially homologous" when they are identical to or not differing in more that 40% of the nucleotides, more preferably about 20% of the nucleotides, and most preferably about 10% of the nucleotides.

A virus that has had a foreign DNA sequence inserted into its genome is a "recombinant virus," while a virus that has had a portion of its genome removed by intentional deletion (e.g., by genetic engineering) is a "mutant virus."

The term "polypeptide" is used in its broadest sense, i.e., any polymer of amino acids (dipeptide or greater) linked through peptide bonds. Thus, the term "polypeptide" includes proteins, oligopeptides, protein fragments, analogs, muteins, fusion proteins, etc.

"Antigenic" refers to the ability of a molecule containing one or more epitopes to stimulate an animal or human immune system to make a humoral and/or cellular antigen-specific response. An "antigen" is an antigenic polypeptide.

An "immunological response" to a composition or vaccine is the development in the host of a cellular and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

The terms "immunogenic polypeptide" and "immunogenic amino acid sequence" refer to a polypeptide or amino acid sequence, respectively, which elicit antibodies that neutralize viral infectivity, and/or mediate antibody-complement or antibody dependent cell cytotoxicity to provide protection of an immunized host. An "immunogenic polypeptide" as used herein, includes the full length (or near full length) sequence of the desired protein or an immunogenic fragment thereof.

By "immunogenic fragment" is meant a fragment of a polypeptide which includes one or more epitopes and thus elicits antibodies that neutralize viral infectivity, and/or mediates antibody-complement or antibody dependent cell cytotoxicity to provide protection of an immunized host. Such fragments will usually be at least about 5 amino acids in length, and preferably at least about 10 to 15 amino acids in length. There is no critical upper limit to the length of the fragment, which could comprise nearly the full length of the protein sequence, or even a fusion protein comprising fragments of two or more of the antigens.

By "infectious" is meant having the capacity to deliver the viral genome into cells.

A "substantially pure" protein will be free of other proteins, preferably at least 10% homogeneous, more preferably 60% homogeneous, and most preferably 95% homogeneous.

BRIEF DESCRIPTION OF THE DRAWING FIGURE

FIG. 1 is a diagram of BAV-1 genomic DNA showing the relative size of various regions in kilobase pairs. Fragments are lettered in order of decreasing size.

DETAILED DESCRIPTION OF THE INVENTION

Throughout this disclosure, various publications, patents and patent applications are referenced. The disclosures of these publications, patents and patent applications are herein incorporated by reference.

The methods and compositions of the present invention involve modifying DNA sequences from various prokaryotic and eucaryotic sources and by gene insertions, gene deletions, single or multiple base changes, and subsequent insertions of these modified sequences into the genome of an adenovirus. One example includes inserting parts of an adenovirus DNA into plasmids in bacteria, reconstructing the virus DNA while in this state so that the DNA contains deletions of certain sequences, and/or furthermore adding foreign DNA sequences either in place of the deletions or at sites removed by the deletions.

Generally, the foreign gene construct is cloned into an adenovirus nucleotide sequence which represents only a part of the entire adenovirus genome, which may have one or more appropriate deletions. This chimeric DNA sequence is usually present in a plasmid which allows successful cloning to produce many copies of the sequence. The cloned foreign gene construct can then be included in the complete viral genome, for example, by in vivo recombination following a DNA-mediated cotransfection technique. Multiple copies of a coding sequence or more than one coding sequences can be inserted into the viral genome so that the recombinant virus can express more than one foreign protein or multiple copies of the same protein. The foreign gene can have additions, deletions or substitutions to enhance expression and/or immunological effects of the expressed protein.

In order for successful expression of the gene to occur, it can be inserted into an expression vector together with a suitable promoter including enhancer elements and polyadenylation sequences. A number of eucaryotic promoter and polyadenylation sequences which provide successful expression of foreign genes in mammalian cells and how to construct expression cassettes, are known in the art, for example in U.S. Pat. No. 5,151,267. The promoter is selected to give optimal expression of immunogenic protein which in turn satisfactorily leads to humoral, cell mediated and mucosal immune responses according to known criteria.

The polypeptide encoded by the foreign DNA sequence is produced by expression in vivo in a recombinant virus-infected cell. The polypeptide may be immunogenic. More than one foreign gene can be inserted into the viral genome to obtain successful production of more than one effective protein.

Therefore, one utility of the use of a mutant adenovirus or the addition of a foreign DNA sequence into the genome of an adenovirus is to vaccinate an animal. For example, a mutant virus could be introduced into an animal to elicit an immune response to the mutant virus.

Alternatively, a recombinant adenovirus having a foreign DNA sequence inserted into its genome that encodes a polypeptide may also serve to elicit an immune response in an animal to the foreign DNA sequence, the polypeptide encoded by the foreign DNA sequence and/or the adenovirus itself. Such a virus may also be used to introduce foreign DNA and its products into the host animal to alleviate a defective genomic condition in the host animal or to enhance the genomic condition of the host animal.

While the present invention is not limited to the use of particular viral vectors, in preferred embodiments the present invention utilizes bovine adenovirus expression vector systems. In particularly preferred embodiments, the present invention comprises a bovine adenovirus in which part or all of the E4 gene region is deleted and/or into which foreign DNA is introduced. Alternatively, the system comprises a bovine adenovirus 1 (BAV-1) in which part or all of the E3 and/or E4 gene regions are deleted and/or into which foreign DNA is introduced.

The present invention is not limited by the foreign genes or coding sequences (viral, prokaryotic, and eukaryotic) that are inserted into a bovine adenovirus nucleotide sequence in accordance with the present invention. Typically the foreign DNA sequence of interest will be derived from pathogens that in bovine cause diseases that have an economic impact on the cattle or dairy industry. The genes may be derived from organisms for which there are existing vaccines, and because of the novel advantages of the vectoring technology, the adenovirus derived vaccines will be superior. Also, the gene of interest may be derived from pathogens for which there is currently no vaccine but where there is a requirement for control of the disease. Typically, the gene of interest encodes immunogenic polypeptides of the pathogen and may represent surface proteins, secreted proteins and structural proteins.

The present invention is not limited by the particular organisms from which a foreign DNA sequence is obtained for gene insertion into a bovine adenovirus genome. In preferred embodiments, the foreign DNA is from bovine rotavirus, bovine coronavirus, bovine herpes virus type 1, bovine respiratory syncytial virus, bovine para influenza virus type 3 (BPI-3), bovine diarrhea virus, bovine rhinotracheitis virus, bovine parainfluenza type 3 virus, *Pasteurella haemolytica, Pasteurella multocida* and/or *Haemophilus somnus*. In another preferred embodiment, the foreign DNA encodes a cytokine.

The present invention is also not limited to the use of a particular DNA sequence from such an organism. Often selection of the foreign DNA sequence to be inserted into an adenovirus genome is based upon the protein it encodes. Preferably, the foreign DNA sequence encodes an immunogenic polypeptide.

The preferred immunogenic polypeptide to be expressed by the virus systems of the present invention contain full-length (or near full-length) sequences encoding antigens. Alternatively, shorter sequences that are immunogenic (i.e., encode one or more epitopes) can be used. The shorter sequence can encode a neutralizing epitope, which is defined as an epitope capable of eliciting antibodies that neutralize virus infectivity in an in vitro assay. Preferably the peptide should encode a protective epitope that is capable of raising in the host an protective immune response; i.e., an antibody-mediated and/or a cell-mediated immune response that protects an immunized host from infection. In some cases the gene for a particular antigen can contain a large number of introns or can be from an RNA virus. In these cases a complementary DNA copy (cDNA) can be used.

It is also possible to use fragments of nucleotide sequences of genes rather than the complete sequence as found in the wild-type organism. Where available, synthetic genes or fragments thereof can also be used. However, the present invention can be used with a wide variety of genes and/or fragment and is not limited to those set out herein.

Thus, the antigens encoded by the foreign DNA sequences used in the present invention can be either native or recombinant immunogenic polypeptides or fragments. They can be partial sequences, full-length sequences, or even fusions (e.g., having appropriate leader sequences for the recombinant host and/or with an additional antigen sequence for another pathogen).

The present invention is also not limited by the ability of the resulting recombinant and mutant viruses to replicate. In a preferred embodiment, the mutant and recombinant viruses of the present invention are replication competent. In this manner, a complimenting cell line is not necessary to produce adequate supplies of virus.

As stated above, the present invention contemplates the administration of the recombinant and mutant viruses of the present invention to vaccinate an animal. The present invention is not limited by the nature of administration to an animal. For example, the antigens used in the present invention, particularly when comprised of short oligopeptides, can be conjugated to a vaccine carrier. Vaccine carriers are well known in the art: for example, bovine serum albumin (BSA), human serum albumin (HSA) and keyhole limpet hemocyanin (KLH). A preferred carrier protein, rotavirus VP6, is disclosed in EPO Pub. No. 0259149.

The vaccines of the present invention carrying foreign genes or fragments can also be orally administered in a suitable oral carrier, such as in an enteric-coated dosage form. Oral formulations include such normally-employed excipients as, for example, pharmaceutical grades of mannitol, lactose, starch, magnesium stearate, sodium saccharin cellulose, magnesium carbonate, etc. Oral vaccine compositions may be taken in the form of solutions (e.g., water), suspensions, tablets, pills, capsules, sustained release formulations, or powders, containing from about 10% to about 95% of the active ingredient, preferably about 25% to about 70%. An oral vaccine may be preferable to raise mucosal immunity in combination with systemic immunity, which plays an important role in protection against pathogens infecting the gastrointestinal tract.

In addition, the vaccine can be formulated into a suppository. For suppositories, the vaccine composition will include traditional binders and carriers, such as polyalkaline glycols or triglycerides. Such suppositories may be formed from mixtures containing the active ingredient in the range of about 0.5% to about 10% (w/w), preferably about 1% to about 2%.

Protocols for administering the vaccine composition(s) of the present invention to animals are within the skill of the art in view of the present disclosure. Those skilled in the art will select a concentration of the vaccine composition in a dose effective to elicit an antibody and/or T-cell mediated immune response to the antigenic fragment.

The timing of administration may also be important. For example, a primary inoculation preferably may be followed by subsequent booster inoculations if needed. It may also be preferred, although optional, to administer a second, booster immunization to the animal several weeks to several months after the initial immunization. To insure sustained high levels of protection against disease, it may be helpful to readminister a booster immunization to the animals at regular intervals, for example once every several years. Alternatively, an initial dose may be administered orally followed by later inoculations, or vice versa. Preferred vaccination protocols can be established through routine vaccination protocol experiments.

The dosage for all routes of administration of an in vivo recombinant virus vaccine depends on various factors, including the size of the patient, the nature of the infection against which protection is needed, the type of carrier and other factors, which can readily be determined by those of skill in the art. By way of non-limiting example, a dosage of between $10^3$ plaque forming units (pfu) and $10^8$ pfu can be used.

The present invention also includes a method for providing gene therapy to a mammal in need thereof to control a gene deficiency. In one embodiment, the methods comprises administering to said mammal a live recombinant bovine adenovirus containing a foreign nucleotide sequence encoding a non-defective form of a gene. The foreign nucleotide sequence is either incorporated into the mammalian genome or is maintained independently to provide expression of the required gene in the target organ or tissue. These kinds of techniques have recently been used by those of skill in the art to replace a defective gene or portion thereof. For example, U.S. Pat. No. 5,399,346 to Anderson et al. describes techniques for gene therapy. Moreover, examples of foreign genes nucleotide sequences or portions thereof that can be incorporated for use in a conventional gene therapy include, but are not limited to, cystic fibrosis transmembrane conductance regulator gene, human minidystrophin gene, alpha 1-antitrypsin gene and others.

Methods for constructing, selecting and purifying recombinant adenovirus are detailed below in the materials, methods and examples below. The following serve to illustrate certain preferred embodiments and aspects of the present invention and are not to be construed as limiting the scope thereof.

Preparation of Bovine Adenovirus (BAV-1) Stock

Bovine adenovirus stocks were prepared by infecting tissue culture cells, Madin-Darby bovine kidney cells (MDBK), at a multiplicity of infection of 0.01 PFU/cell in Dulbecco's Modified Eagle Medium (DMEM) containing 2 mM glutamine, 100 units/ml penicillin, 100 units/ml streptomycin (these components are obtained from Sigma (St. Louis, Mo.) or an equivalent supplier, and hereafter are referred to as complete DME medium) plus 1% fetal bovine serum. After cytopathic effect was complete, the medium and cells were harvested. After one or two cycles of freezing (−70° C.) and thawing (37° C.), the infected cells were aliquot as 1 ml stock and stored frozen at −70° C.

Preparation of Bovine Adenovirus (BAV-1) DNA

All manipulations of bovine adenovirus were made using strain 10 (ATCC VR-313). For the preparation of BAV-1 viral DNA from the cytoplasm of infected cells, MDBK cells were infected at a multiplicity of infection (MOI) sufficient to cause extensive cytopathic effect before the cells overgrew. All incubations were carried out at 37° C. in a humidified incubator with 5% $CO_2$ in air.

The best DNA yields were obtained by harvesting monolayers which were maximally infected, but showing incomplete cell lysis (typically 5–7 days). Infected cells were harvested by scraping the cells into the medium using a cell scraper (Costar brand). The cell suspension was centrifuged at 3000 rpm for 10 minutes at 5° C. in a GS-3 rotor (Sorvall Instruments, Newtown, Conn.). The resultant pellet was resuspended in cold PBS (20 ml/Roller Bottle) and subjected to another centrifugation for 10 minutes at 3000 rpm in the cold.

After decanting the PBS, the cellular pellet was resuspended in 5 ml/roller bottle of TE buffer (10 mM Tris pH 7.5 and 1 mM EDTA) and swell on ice for 15 minutes. NP40 (Nonidet P-40.TM.; Sigma, St. Louis, Mo.) was added to the sample to a final concentration of 0.5% and keep on ice for another 15 minutes. The sample was centrifuged for 10 minutes at 3000 rpm in the cold to pellet the nuclei and remove cellular debris.

The supernatant fluid was carefully transferred to a 30 ml Corex centrifuge tube. SDS (sodium dodecyl sulfate; stock 20%) were added to the sample to final concentrations of 1%. 200 μl of proteinase-K at 10 mg/ml (Boehringer Mannheim, Indianapolis, Ind.) was added per roller bottle of sample, mixed, and incubated at 45° C. for 1–2 hours.

After this period, an equal volume of water-saturated phenol was added to the sample and mixed by vortex. The sample was spun in a clinical centrifuge for 5 minutes at 3000 rpm to separate the phases. NaAc was added to the aqueous phase to a final concentration of 0.3M (stock solution 3M pH 5.2), and the nucleic acid precipitated at −70° C. for 30 minutes after the addition of 2.5 volumes of cold absolute ethanol. DNA in the sample was pelleted by spinning for 20 minutes to 8000 rpm in an HB-4 rotor at 4° C.

The supernatant was carefully removed and the DNA pellet washed once with 25 ml of 80% ethanol. The DNA pellet was dried briefly by vacuum (2–3 minutes), and resuspended in 2 ml/roller bottle of infected cells of TE buffer (20 mM Tris pH 7.5, 1 mM EDTA). 10 μl of RNaseA at 10 mg/ml (Sigma, St. Louis, Mo.) was added and incubate at 37° C. for one hour. 0.5 ml of 5N NaCl and 0.75 ml of 30% PEG was added and precipitated at 4° C. overnight.

DNA in the sample was pelleted by spinning for 20 minutes to 8000 rpm in an HB-4 rotor at 4° C. Resuspend pellet in 2 ml TES buffer (20 mM Tris pH7.5, 1 mM EDTA and 0.2% SDS) and extracted with an equal volume of water-saturated phenol. The sample was spun in a clinical centrifuge for 5 minutes at 3000 rpm to separate the phases. NaAc was added to the aqueous phase to a final concentration of 0.3M (stock solution 3M pH 5.2), and the nucleic acid precipitated at −70° C. for 30 minutes after the addition of 2.5 volumes of cold absolute ethanol.

DNA in the sample was pelleted by spinning for 20 minutes to 8000 rpm in an HB-4 rotor at 5° C. The supernatant was carefully removed and the DNA pellet washed once with 25 ml of 80% ethanol. The DNA pellet was dried briefly by vacuum (2–3 minutes), and resuspended in 200 μl/roller bottle of infected cells of TE buffer (10 mM Tris pH 7.5, 1 mM EDTA). All viral DNA was stored at approximately 4° C.

Molecular Biological Techniques

Techniques for the manipulation of bacteria and DNA, including such procedures as digestion with restriction endonucleases, gel electrophoresis, extraction of DNA from gels, ligation, phosphorylation with kinase, treatment with phosphatase, growth of bacterial cultures, transformation of bacteria with DNA, and other molecular biological methods are described by Maniatis et al. (T. Maniatis, et al., Molecular Cloning: *A Laboratory Manual*, Cold Spring Harbor, N.Y. (1982)) and Sambrook et al. (J. Sambrook, et al., *Molecular Cloning: A Laboratory Manual Second Edition*, Cold Spring Harbor Press, Cold Spring Harbor, N.Y. (1989)). The polymerase chain reaction (PCR) was used to introduce restriction sites convenient for the manipulation of various DNAs. The procedures used are described by Innis et al (M. A. Innis, et al., PCR Protocols: A Guide To Methods And Applications, pp. 84–91, Academic Press, Inc., San Diego, Calif. (1990)).

In general, amplified fragments were less than 2000 base pairs in size and critical regions of amplified fragments were confirmed by DNA sequencing. Except as noted, these techniques were used with minor variations.

DNA Sequencing

DNA sequencing was performed on the Applied Biosystems Automated Sequencer Model 373A (with XL upgrade) per instructions of the manufacturer. Subclones were made to facilitate sequencing. Internal primers were synthesized on an ABI 392 DNA synthesizer or obtained commercially (Genosys Biotechnologies, Inc., The Woodlands, Tex.). Larger DNA sequences were built utilizing consecutive overlapping primers. Sequence across the junctions of large genomic subclones was determined directly using a full length genomic clone as template Assembly, manipulation and comparison of sequences was performed with DNAstar programs. Comparisons with GenBank were performed using NCBI BLAST programs (Altschul, Stephen F., Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs", *Nucleic Acids Res.* 25:3389–3402.).

Construction of Recombinant BAV-1 Genomes in *E. coli*

Recombinant BAV-1 genomes are constructed by homologous recombination according to the method of C. Chartier et al (1996) *J. of Virology* 70:805–4810.

A small, easily manipulated plasmid was constructed containing approximately 1000 base pairs each of the Left and Right ends of the BAV-1 genome. Homologous recombination between this vector and BAV-1 genomic DNA results in a plasmid containing the entire BAV-1 genome (adenoviral backbone vector). This BAV-1 genomic plasmid may be used to generate recombinant genomes by linearization of the plasmid and recombination with homology DNAs engineered to contain foreign DNA flanked by DNA derived from the desired BAV-1 insertion site. Note that in order to linearize the adenoviral backbone vector, an infrequent cutting enzyme must be located within the region analogous to the flanking BAV-1 sequences.

We have mapped the restriction sites of such an enzyme. PvuI cuts the BAV-1 genome at two locations one in the BamH1 D fragment and one in the BamH1 C fragment (see FIG. 1). The adenoviral backbone vector contains a third PvuI site within the antibiotic resistance gene of the plasmid. The PvuI site within the BamH1 C fragment is suitable for gene insertion sites within both the E3 and E4 regions. Therefore a partial PvuI digestion of the adenoviral backbone vector will yield a sub population of molecules linearized at the PvuI site in the BamH1 C fragment. These molecules may recombine with the homology DNA to generate a viable plasmid. Molecules linearized at the other two sites will not be able to recombine to generate viable plasmids.

The high competence of bacteria cells E. coli BJ5183 recBC sbcBC (D. Hanahan (1983) *J. Mol. Biol.* 166:557–580) is desired to achieve efficient recombination. Typically, 10 nanograms of a restriction fragment containing foreign DNA flanked by the appropriate BAV insertion sequences (homology DNA) is mixed with 1 nanogram of linearized adenoviral backbone vector in a total volume of 10 μl. Fifty microliters of competent BJ5183 cells were added. After 15 min. on ice, 5 min. at 37° C. and 15 min. on ice, 200 μl of LB was added and the cells plated on agar containing LB+ 80 μg/ml carbenicillin, after one hour at 37° C.

Low temperature (25–27° C.) for growing small scale cultures (for screening carbenicillin resistant colonies) and subsequent large scale cultures (for isolation of large quantities of plasmid DNA) is essential. $Carb^R$ colonies were first grown in 4–5 ml cultures at 25–27° C. for two days. Small scale DNAs were prepared using boiling method (J. Sambrook, et al., *Molecular Cloning: A Laboratory Manual Second Edition*, Cold Spring Harbor Press, Cold Spring Harbor, N.Y. (1989)) and analyzed by DNA restriction analysis. To purify the DNA away from vector DNA concatemers the DNAs from correct clones were re-transform into DH10B (Life Technologies) cells. Analysis of bacterial colonies by DNA restriction analysis was repeated. Glycerol stocks were prepared from the correct clones and stored at −70° C. Large quantities of plasmid DNA were prepared using Qiagen Plasmid Kit (Qiagen Inc.) or scale-up of boiling method from 250 ml cultures which were inoculated with glycerol stock and grown at 37° C. for one day.

Transfection of BAV-1 DNA

Approximately $1.5 \times 10^5$ cells/ml (MDBK) were plated in 6 cm plates 24 hr before transfection, by which time they reached 50–70% confluency. For transfection the Lipofectin method was used according to the manufacturer's instructions (Lipofectin, Life Technologies, Rockville, Md.). A transfection mix was prepared by adding several (4–15) μg of BAV-1 viral DNA or linearized genome plasmid DNA and 50 μl of Lipofectin Reagent to 200 μl of serum-free medium according to the manufacturer's instruction.

After incubation at room temperature for 15–30 min, the transfection mix was added to the cells. After 4–6 hr at 37° C., the media containing the transfection mix was removed, and 5 ml of growth medium was added. Cytopathic effect became apparent within 7–10 days. The transfected virus stock was harvested by scraping cells in the culture and stored at −70° C.

Plaque Purification of Recombinant Constructs

Monolayers of MDBK cells in 6 cm or 10 cm plates were infected with transfection stock, overlaid with nutrient agarose media and incubated for 5–10 days at 37° C. Once plaques have developed, single and well-isolated plaque was picked onto MDBK cells. After 5–10 days when 80–90% cytopathic effect was reached, the infected cells (P1 stock) were harvested and stored at −70° C. This procedure was repeated one more time with P1 stock.

Cloning of Bovine Viral Diarrhea Virus (BVDV) Glycoprotein 53 (g53) Gene

The bovine viral diarrhea g53 gene was cloned by a PCR cloning procedure essentially as described by Katz et al. (*Journal of Virology* 64: 1808–1811 (1990)) for the HA gene of human influenza. Viral RNA prepared from BVD virus Singer strain grown in MDBK cells was first converted to cDNA utilizing an oligonucleotide primer specific for the target gene. The cDNA was then used as a template for polymerase chain reaction (PCR) cloning (M. A. Innis et al., PCR Protocols: A Guide to Methods and Applications, 84–91, Academic Press, Inc. San Diego (1990)) of the targeted region. The PCR primers were designed to incorporate restriction sites which permit the cloning of the amplified coding regions into vectors containing the appropriate signals for expression in BAV-1. One pair of oligonucleotides were required for the coding region. The g53 gene coding region (amino acids 1–394) from the BVDV Singer strain (M. S. Collett et al., *Journal of Virology* 65, 200–208, (1988)) was cloned using the following primers: 5'-CTTGGATCCTCATCCATACTGAGTCCCTGAGG CCTTCTGTTC-3' [SEQ ID NO: 1] for cDNA priming and combined with 5'-CATAGATCTTGTGGTGCTGTCCGACTTCGCA-3' [SEQ ID NO: 2] for PCR.

Western Blotting Procedure

Samples of lysates and protein standards were run on a polyacrylamide gel according to the procedure of Laemnli, *Nature* 227, 680–685 (1970)). After gel electrophoresis the proteins were transferred and processed according to Sambrook, et al., *Molecular Cloning A Laboratory Manual Second Edition*, Cold Spring Harbor Press, Cold Spring Harbor, N.Y. (1989). The primary antibody was a mouse monoclonal antibody (Mab 6.12.2 from Dubovi, Cornell University, Ithaca, N.Y.) diluted 1:100 with 5% non-fat dry milk in Tris-sodium chloride, and sodium Azide (TSA: 6.61 g Tris-HCl, 0.97 g Tris-base, 9.0 g NaCl and 2.0 g Sodium Azide per liter H2O). The secondary antibody was a goat anti-mouse alkaline phosphatase conjugate diluted 1:1000 with TSA.

Plasmid 990-11

Plasmid 990-11 contains the Left and Right ends of the BAV-1 genome. These sequences were cloned by standard PCR methods (M. A. Innis, et al., PCR Protocols: A Guide To Methods And Applications, pp. 84–91, Academic Press, Inc., San Diego, Calif. (1990) using primers based on the sequences determined for the EcoR1 A and BamH1 F fragments respectively. Primers (1) 5'-3' GGCCTTAATTAACATCATCAATAATATACGGAACAC [SEQ ID NO: 5] and (2) 5'-3' GGAAGATCTTGAGCATGCAGAGCAATTCACGCCGGGTAT [SEQ ID NO: 6] were used to PCR the Left end of BAV-1. Since three repetitive elements within this region shared the same 5' end sequences (i.e. primer 1), 1760 bp, 1340 bp and 920 bp BAV-1 DNA fragments were amplified by PCR. The 920 bp DNA fragment was cloned into PCR-Blunt vector (Invitrogen, Carlsbad, Calif.). Primers (1) and (3) 5'-GGCAATGAGATCTTTTGGATGACAAGCTGAGC TACGCG-3' [SEQ ID NO: 7] were used to PCR the Right end of BAV-1, 740 bp and 1160 bp PCR products were amplified and 1160 bp fragment DNA was cloned into pCR-Blunt vector (Invitrogen, Carlsbad, Calif.). Plasmid 990-11 was then constructed by cloning the BAV-1 end fragments into the polylinker of plasmid pPolyII (R. Lathe, J. L. Vilotte, and A. J. Clark, *Gene,* 57:193–201, 1997). The end fragments were cloned as a single PacI fragment containing a unique Bg/II site at their internal junction. Only the BamH1 and EcoR1 sites were retained from the polylinker.

Plasmid 990-50 (Adenoviral Backbone Vector)

Plasmid 990-50 was constructed according to the method described above (Construction of Recombinant BAV-1 Genomes in *E. coli*). Briefly, co-transformation of the Bg/II-linearized plasmid 990-11 and BAV-1 genomic DNA regenerated a stable circular plasmid containing the entire BAV-1 genome. In this plasmid PacI sites flank the inserted BAV-1 genomic sequences. As PacI is absent from BAV-1 genomic DNA, digestion with this enzyme allows the precise excision of the full-length BAV-1 genome from the plasmid 990-50.

Plasmid 996-80D

Plasmid 996-80D contains DNA encompassing approximately 5945 base pairs of the Right end of the BAV-1 genome from which the EcoR1 "G" and "H" fragments have been deleted and replaced with a synthetic SmaI site. The plasmid was constructed for the purpose of deleting a portion of the BAV-1 E4 region. It may also be used to insert foreign DNA into recombinant BAV-1 genomes. It contains a unique SmaI restriction enzyme site into which foreign DNA may be inserted. The plasmid may be constructed utilizing standard recombinant DNA techniques (see above Molecular Biological Techniques) by joining restriction fragments from the following sources with the synthetic DNA sequences indicated. The plasmid vector is derived from an approximately 2774 base pair HindIII to PvuII restriction fragment of pSP64 (Promega Corporation, Madison, Wis.). The synthetic linker sequence 5'-CTGTAGATCTGCGGCCGCGTTTAAACGTCGAC AGCTTCCC-3' [SEQ ID NO: 8] is ligated to the PvuII site of pSP64 (Promega Corporation, Madison, Wis.). Fragment 1 is an approximately 1693 base pair PstI to EcoR1 sub fragment of the BAV-1 BamH1 "C" fragment (positions 28241 to 29933 from SEQ ID NO: 3). The synthetic linker sequence 5'-AATTCGAGCTCGCCCGGGCGAGCTCGA-3' [SEQ ID NO: 9] is ligated to fragment 1 retaining EcoR1 sites at both ends of the linker sequence. Fragment 2 is an approximately 48 base pair EcoR1 to BamH1 restriction sub fragment of the BAV-1 BamH1 "C" fragment (positions 31732 to 31779 from SEQ ID NO: 3). Fragment 3 is the approximately 2406 base pair BAV-1 BamH1 "F" fragment (positions 31780 to 34185 from SEQ ID NO: 3). The synthetic linker sequence 5'-GACTCTAGGGGCGGGGAGTTTAAACGCGGCCG CAGATCTAGCT-3' [SEQ ID NO: 10] is ligated between fragment 3 and the HindIII site of pSP64 (Promega Corporation, Madison, Wis.). Note that the BAV-1 sequences can be cut out of this plasmid via the NotI restriction sites located in the flanking synthetic linker sequences.

Plasmid 1004-73.16.14

Plasmid 1004-73.16.14 contains a recombinant BAV-1 genome from which the EcoR1 "G" and "H" fragments have been deleted and replaced by a synthetic SmaI site (5'-GAATTCGAGCTCGCCCGGGCGAGCTCGAATTC-3') [SEQ ID NO: 11]. This plasmid may be used to generate recombinant bovine adenovirus vectors with deletion and gene insertions at the E4 region. The plasmid may be constructed according to the method above (Construction of Recombinant BAV-1 Genomes in *E. coli*). The homology DNA is derived from the NotI insert of plasmid 996-80D and the adenoviral backbone vector plasmid 990-50 is linearized by partial digestion with the PvuI.

Plasmid 1004-07.16

Plasmid 1004-07.16 was constructed by inserting a BVDV g53 gene, engineered to be under control of the human cytomegalovirus immediate early promoter (Invitrogen, Carlsbad, Calif.), into the unique SmaI site of plasmid 996-80D. The BVDV g53 gene was isolated according to the method above (Cloning of Bovine Viral Diarrhea virus g53 gene).

Plasmid 1004-40

Plasmid 1004-40 contains a recombinant BAV-1 genome from which the EcoR1 G and H fragments have been deleted. The gene for the bovine viral diarrhea virus (BVDV) glycoprotein 53 (g53) (amino acids 1–394) under the control of the HCMV immediate early promoter was inserted into the deleted region. The plasmid may be constructed according to the method above (Construction of Recombinant BAV-1 Genomes in *E. coli*). The homology DNA is derived from the NotI insert of plasmid 1004-17.16 and the adenoviral backbone vector plasmid 990-50 is linearized by partial digestion with the PvuI.

Plasmid 1018-14.2

Plasmid 1018-14.2 contains DNA flanking the E3 region of BAV-1, from which a specific region of this sequence flanked by SalI and BamH1 sites (positions 25664 to 26840 from SEQ ID NO: 3) has been deleted. The plasmid was constructed for the purpose of deleting the corresponding portion of the BAV-1 E3 region. It may also be used to insert foreign DNA into recombinant BAV-1 genomes. It contains a unique HindIII restriction enzyme site into which foreign DNA may be inserted. The plasmid may be constructed utilizing standard recombinant DNA techniques (see above Molecular Biological Techniques) by joining restriction fragments from the following sources with the synthetic DNA sequences indicated. The plasmid vector is derived from an approximately 2774 base pair HindIII to PvuII restriction fragment of pSP64 (Promega Corporation, Madison, Wis.). The synthetic linker sequence 5'-CTGTAGATCTGCGGCCGCGTTTAAACG-3' [SEQ ID NO: 12] is ligated to the PvuII site of pSP64 (Promega Corporation, Madison, Wis.). Fragment 1 is an approximately 2665 base pair SalI to SalI sub fragment (positions 22999 to 25663 from SEQ ID NO: 3) of the BAV-1 BamHI B fragment. Fragment 1 is ligated to the upstream synthetic sequence retaining the SalI site at the junction. Fragment 1 contains a unique AvaI site (positions 25317 to 25322 from SEQ ID NO: 3). Fragment 1 is oriented such that the unique AvaI site is closer (406 base pairs) to fragment 2 than to the plasmid vector. The synthetic linker sequence 5'-TCGACAAGCTTCCC-3' [SEQ ID NO: 13] is ligated to second end of fragment 1 again retaining the SalI site at the junction. Fragment 2 is an approximately 4223 base pair BamH1 to HindIII restriction sub fragment of the BAV-1 BamH1 C fragment (positions 26851 to 31073 from SEQ ID NO: 3). Note that the end of both fragments were blunt end by treatment with T4 polymerase. The synthetic linker sequence 5'-CCCGGGAGTTTAAACGCGGCCGCAGATCTAGCT-3' [SEQ ID NO: 14] is ligated between fragment 2 and the HindIII site of pSP64 (Promega Corporation, Madison, Wis.). Note that the HindIII site is not retained. The BAV-1 sequences can be cut out of this plasmid via the NotI restriction sites located in the flanking synthetic linker sequences.

Plasmid 1018-75

Plasmid 1018-75 contains a recombinant BAV-1 genome from which a specific region of the BamH1 "B" fragment (positions 25664 to 26840 from SEQ ID NO: 3) has been deleted. This plasmid may be used to generate recombinant bovine adenovirus vectors with deletions and gene insertions at the E3 region. The plasmid may be constructed according to the method above (Construction of Recombinant BAV-1 Genomes in *E. coli*). The homology DNA is derived from the NotI insert of plasmid 1018-14.2 and the adenoviral backbone vector plasmid 990-50 is linearized by partial digestion with the PvuI.

Plasmid 1018-23C15

Plasmid 1018-23C15 was constructed by inserting a BVDV g53 gene, engineered to be under control of the human cytomegalovirus immediate early promoter (Invitrogen, Carlsbad, Calif.), into the unique HindIII site of plasmid 1018-14.2. The BVDV g53 gene was isolated according to the method above (Cloning of Bovine Viral Diarrhea virus g53 gene).

Plasmid 1018-42

Plasmid 1018-42 contains a recombinant BAV-1 genome from which a specific region of the BamH1 "B" fragment (positions 25664 to 26840 from SEQ ID NO: 3) has been deleted. The gene for the bovine viral diarrhea virus (BVDV) glycoprotein 53 (g53) (amino acids 1–394) under the control of the HCMV immediate early promoter was inserted into the deleted region. The plasmid may be constructed according to the method above (Construction of Recombinant BAV-1 Genomes in E. coli). The homology DNA is derived from the NotI insert of plasmid 1018-23C15 and the adenoviral backbone vector plasmid 990-50 is linearized by partial digestion with the PvuI.

Plasmid 1018-45

Plasmid 1018-45 contains DNA flanking the E3 region of BAV-1, from which a specific region of this sequence flanked by EcoR1 and BamH1 sites (positions 25765 to 26850 from SEQ ID NO: 3) has been deleted. The plasmid was constructed for the purpose of deleting the corresponding portion of the BAV-1 E3 region. It may also be used to insert foreign DNA into recombinant BAV-1 genomes. It contains a unique HindIII restriction enzyme site into which foreign DNA may be inserted. The plasmid may be constructed utilizing standard recombinant DNA techniques (see above Molecular Biological Techniques) by joining restriction fragments from the following sources with the synthetic DNA sequences indicated. The plasmid vector is derived from an approximately 2774 base pair HindlIII to PvuII restriction fragment of pSP64 (Promega Corporation, Madison, Wis.). The synthetic linker sequence 5'-CTGTAGATCTGCGGCCGCGTTTAAACG-3' [SEQ ID NO: 12] is ligated to the PvuII site of pSP64 (Promega Corporation, Madison, Wis.). Fragment 1 is an approximately 1582 base pair SacI to EcoR1 sub fragment (positions 24183 to 25764 from SEQ ID NO: 3) of the BAV-1 BamHI B fragment. Fragment 1 is ligated to the upstream synthetic sequence. The fragment was blunted end with T4 polymerase treatment so neither the SacI nor EcoR1 sites are retained. Fragment 1 contains a unique AvaI site (positions 25317 to 25322 from SEQ ID NO: 3). Fragment 1 is oriented such that the unique AvaI site is closer (406 base pairs) to fragment 2 than to the plasmid vector. The synthetic linker sequence 5'-CAAGCTTCCC-3' [SEQ ID NO: 17] is ligated to second end of fragment 1 again retaining the SalI site at the junction. Fragment 2 is an approximately 4223 base pair BamH1 to HindIII restriction sub fragment of the BAV-1 BamH1 C fragment (positions 26851 to 31073 from SEQ ID NO: 3). Note that the end of both fragments were blunt end by treatment with T4 polymerase. The synthetic linker sequence 5'-CCCGGGAGTTTAAACGCGGCCGCAGATCTAGCT-3' [SEQ ID NO: 14] is ligated between fragment 2 and the HindIII site of pSP64 (Promega Corporation, Madison, Wis.). Note that the HindIII site is not retained. The BAV-1 sequences can be cut out of this plasmid via the NotI restriction sites located in the flanking synthetic linker sequences.

Plasmid 1028-03

Plasmid 1028-03 contains a recombinant BAV-1 genome from which a specific region of the BamH1 "B" fragment (positions 25765 to 26850 from SEQ ID NO: 3) has been deleted. This plasmid may be used to generate recombinant bovine adenovirus vectors with deletions and gene insertions at the E3 region. The plasmid may be constructed according to the method above (Construction of Recombinant BAV-1 Genomes in E. coli). The homology DNA is derived from the NotI insert of plasmid 1018-45 and the adenoviral backbone vector plasmid 990-50 is linearized by partial digestion with the PvuI.

Plasmid 1028-77

Plasmid 1028-77 was constructed by inserting a BVDV g53 gene, engineered to be under control of the human cytomegalovirus immediate early promoter (Invitrogen, Carlsbad, Calif.), into the unique HindIII site of plasmid 1018-45. The BVDV g53 gene was isolated according to the method above (Cloning of Bovine Viral Diarrhea virus g53 gene).

Plasmid 1038-16

Plasmid 1038-16 contains a recombinant BAV-1 genome from which a specific region of the BamH1 "B" fragment (positions 25765 to 26850 from SEQ ID NO: 3) has been deleted. The gene for the bovine viral diarrhea virus (BVDV) glycoprotein 53 (g53) (amino acids 1–394) under the control of the HCMV immediate early promoter was inserted into the deleted region. The plasmid may be constructed according to the method above (Construction of Recombinant BAV-1 Genomes in E. coli. The homology DNA is derived from the NotI insert of plasmid 1028-77 and the adenoviral backbone vector plasmid 990-50 is linearized by partial digestion with the PvuI.

Plasmid 1054-93

Plasmid 1054-93 contains DNA derived from the E4 region of BAV-1. The sequence corresponding to positions 33614 to 33725 from SEQ ID NO: 3 has been deleted and replaced with a synthetic PstI site. The plasmid was constructed for the purpose of deleting a portion of the BAV-1 E4 region. It may also be used to insert foreign DNA into recombinant BAV-1 genomes. It contains a unique PstI restriction enzyme site into which foreign DNA may be inserted. The plasmid may be constructed utilizing standard recombinant DNA techniques (see above Molecular Biological Techniques) by joining restriction fragments from the following sources with the synthetic DNA sequences indicated. Note that fragments derived from BAV-1 DNA are ligated in the orientation indicated by the positions given for each fragment. The plasmid vector is derived from an approximately 2774 base pair HindIII to PvuII restriction fragment of pSP64 (Promega Corporation, Madison, Wis.). The synthetic linker sequence 5'-CTGTAGATCTGCGGCCGCGTTTAAACGTCGAC AAGCTTCCC-3' [SEQ ID NO: 8] is ligated to the PvuII site of pSP64 (Promega Corporation, Madison, Wis.). Fragment 1 is an approximately 3538 base pair PstI to BamHI sub fragment of the BAV-1 BamHI "C" fragment positions 28241 to 31779 from SEQ. ID NO.3. Fragment 1 is ligated to the 3' end of the synthetic linker sequence [SEQ ID NO: 8]. Fragment 2 is an approximately 1832 base pair PCR fragment containing sequences derived from the BAV-1 genome (positions 31780 to 33613 from SEQ ID NO: 3). Fragment 2 is ligated to fragment 1 such that the BamHI site at the junction is retained. The synthetic linker sequence 5'-CTGCAG-3+ [SEQ ID NO: 4] is ligated to fragment 2. Fragment 3 is an approximately 460 base pair PCR fragment containing sequences derived from the BAV-1 genome (positions 33725 to 34185 from SEQ ID NO: 3). Fragment 3 is ligated to the 3' end of the synthetic linker sequence 5'-CTGCAG-3'. The synthetic linker sequence 5'-GACTCTAGGGGCGGGGAGTTTAAACGCGGC CGCAGATCTAGCT-3' [SEQ ID NO: 10] is ligated between fragment 3 and the HindIII site of pSP64 (Promega Corporation, Madison, Wis.). Note that the BAV-1 sequences can be cut out of this plasmid via the NotI restriction sites located in the flanking synthetic linker sequences.

Plasmid 1055-38

Plasmid 1055-38 contains DNA derived from the E4 region of BAV-1. The sequence encoding nORF13 (see Table 1) has been deleted and replaced with a synthetic PstI site. The plasmid was constructed for the purpose of deleting a portion of the BAV-1 E4 region. It may also be used to insert foreign DNA into recombinant BAV-1 genomes. It contains a unique PstI restriction enzyme site into which foreign DNA may be inserted. The plasmid may be constructed utilizing standard recombinant DNA techniques (see above Molecular Biological Techniques) by joining DNA fragments from the following sources with the synthetic DNA sequences indicated. Note that fragments derived from BAV-1 DNA are ligated in the orientation indicated by the positions given for each fragment. The plasmid vector is derived from an approximately 2774 base pair HindIII to PvuII restriction fragment of pSP64 (Promega Corporation, Madison, Wis.). The synthetic linker sequence 5'-CTGTAGATCTGCGGCCGCGTTTAAACGTCGA CAAGCTTCCC-3' [SEQ ID NO: 8] is ligated to the PvuII site of pSP64 (Promega Corporation, Madison, Wis.). Fragment 1 is an approximately 1282 base pair PCR fragment containing sequences derived from the BAV-1 genome (positions 28240 to 29522 from SEQ ID NO: 3). Fragment 1 is ligated to the 3' end of the synthetic linker sequence indicated above [SEQ ID NO: 8]. The synthetic linker sequence 5'-CTGCAG-3' [SEQ ID NO: 4] is ligated to fragment 1. Fragment 2 is an approximately 1372 base pair PCR fragment containing sequences derived from the BAV-1 genome (positions 30407 to 31779 from SEQ ID NO: 3). Fragment 2 is ligated to the 3' end of the synthetic linker sequence 5'-CTGCAG-3' [SEQ ID NO: 4]. Fragment 3 is the approximately 2406 base pair BAV-1 BamH1 "F" fragment (positions 31779 to 34185 from SEQ ID NO: 3). Fragment 3 is ligated to the 3' end of fragment 2. The synthetic linker sequence 5'-GACTCTAGGGGCGGGGAGTTTAAACGCGGCC GCAGATCTAGCT-3' [SEQ ID NO: 10] is ligated between fragment 3 and the HindIII site of pSP64 (Promega Corporation, Madison, Wis.). Note that the BAV-1 sequences can be cut out of this plasmid via the NotI restriction sites located in the flanking synthetic linker sequences.

Plasmid 1055-52

Plasmid 1055-52 contains a recombinant BAV-1 genome from which a portion of the E4 region (positions 29522–30407 from SEQ ID NO: 3) has been deleted and replaced by a synthetic PstI site (5'-CTGCAG-3') [SEQ ID NO: 4]. This plasmid may be used to generate recombinant bovine adenovirus vectors with gene insertions and/or a deletion at the E4 region. The plasmid may be constructed according to the method above (Construction of Recombinant BAV-1 Genomes in E. coli). The homology DNA is derived from the NotI insert of plasmid 1055-38 and the adenoviral backbone vector plasmid 990-50 is linearized by partial digestion with the PvuI.

Plasmid 1055-47

Plasmid 1055-47 was constructed by inserting a BVDV g53 gene into the unique PstI site of plasmid 1055-38. The BVDV coding region was inserted in the reverse complimentary orientation such that it is transcribed by the E4 region promoter located at the right end of the genome. The BVDV g53 gene was isolated according to the method above (Cloning of Bovine Viral Diarrhea virus g53 gene).

Plasmid 1055-56

Plasmid 1055-56 contains a recombinant BAV-1 genome from which the BAV-1's sequence from positions 29522 to 30407 [SEQ ID NO: 3] has been deleted. The gene for the BVDV g53 (amino acids 1–394) was inserted into the deleted region. The plasmid may be constructed according to the method above (Construction of Recombinant BAV-1 Genomes in E. coli). The homology DNA is derived from the NotI insert of plasmid 1055-47 and the adenoviral backbone vector plasmid 990-50 is linearized by partial digestion with the PvuI.

Plasmid 1055-93

Plasmid 1055-93 contains DNA derived from the E4 region of BAV-1. The sequence encoding nORF13 (see Table 1) has been deleted and replaced with a synthetic PstI site. The plasmid was constructed for the purpose of deleting a portion of the BAV-1 E4 region. It may also be used to insert foreign DNA into recombinant BAV-1 genomes. It contains a unique PstI restriction enzyme site into which foreign DNA may be inserted. The plasmid may be constructed utilizing standard recombinant DNA techniques (see above Molecular Biological Techniques) by joining DNA fragments from the following sources with the synthetic DNA sequences indicated. Note that fragments derived from BAV-1 DNA are ligated in the orientation indicated by the positions given for each fragment. The plasmid vector is derived from an approximately 2774 base pair HindIII to PvuII restriction fragment of pSP64 (Promega Corporation, Madison, Wis.). The synthetic linker sequence 5'-CTGTAGATCTGCGGCCGCGTTTAAACGTCGA CAAGCTTCCC-3' [SEQ ID NO: 8] is ligated to the PvuII site of pSP64 (Promega Corporation, Madison, Wis.). Fragment 1 is an approximately 1282 base pair PCR fragment containing sequences derived from the BAV-1 genome (positions 28240 to 29522 from SEQ ID NO: 3). Fragment 1 is ligated to the 3' end of the synthetic linker sequence indicated above [SEQ ID NO: 8]. The synthetic linker sequence 5'-CTGCAG-3' [SEQ ID NO: 4] is ligated to fragment 1. Fragment 2 is an approximately 1372 base pair PCR fragment containing sequences derived from the BAV-1 genome (positions 30403 to 31779 from SEQ ID NO: 3). Fragment 2 is ligated to the 3' end of the synthetic linker sequence 5'-CTGCAG-3' [SEQ ID NO: 4]. Fragment 3 is the approximately 2406 base pair BAV-1 BamH1 "F" fragment (positions 31779 to 34185 from SEQ ID NO: 3). Fragment 3 is ligated to the 3' end of fragment 2. The synthetic linker sequence 5'-GACTCTAGGGGCGGGGAGTTTAAACGCGGCC GCAGATCTAGCT-3' [SEQ ID NO: 10] is ligated between fragment 3 and the HindIII site of pSP64 (Promega Corporation, Madison, Wis.). Note that the BAV-1 sequences can be cut out of this plasmid via the NotI restriction sites located in the flanking synthetic linker sequences.

Plasmid 1064-26

Plasmid 1064-26 contains a recombinant BAV-1 genome from which a portion of the E4 region (positions 33613 to 33725 from SEQ ID NO: 3) has been deleted and replaced by a synthetic PstI site (5'-CTGCAG-3') [SEQ ID NO: 4]. The plasmid may be constructed according to the method above (Construction of Recombinant BAV-1 Genomes in E. coli). The homology DNA is derived from the NotI insert of plasmid 1054-93 and the adenoviral backbone vector plasmid 990-50 is linearized by partial digestion with the PvuI.

Plasmid 1066-29

Plasmid 1066-29 was constructed by inserting a BVDV g53 gene into the unique PstI site of plasmid 1055-93. The BVDV coding region was inserted in the reverse complimentary orientation such that it is transcribed by the E4 region promoter located at the right end of the genome. The BVDV g53 gene was isolated according to the method above (Cloning of Bovine Viral Diarrhea virus g53 gene).

Plasmid 1066-44

Plasmid 1066-44 contains a recombinant BAV-1 genome from which a portion of the E4 region (positions 29523 to 30403 from SEQ ID NO: 3) has been deleted and replaced by a synthetic PstI site (5'-CTGCAG-3') [SEQ ID NO: 4]. This plasmid may be used to generate recombinant bovine adenovirus vectors with gene insertions and/or a deletion at the E4 region. The plasmid may be constructed according to the method above (Construction of Recombinant BAV-1 Genomes in E. coli). The homology DNA is derived from the NotI insert of plasmid 1055-93 and the adenoviral backbone vector plasmid 990-50 is linearized by partial digestion with the PvuI.

Plasmid 1066-51

Plasmid 1066-51 contains a recombinant BAV-1 genome from which the BAV-1's sequence from positions 30403 to 29523 [SEQ ID NO: 3] has been deleted. The gene for the BVDV g53 (amino acids 1–394) was inserted into the deleted region. The plasmid may be constructed according to the method above (Construction of Recombinant BAV-1 Genomes in E. coli). The homology DNA is derived from the NotI insert of plasmid 1066-29 and the adenoviral backbone vector plasmid 990-50 is linearized by partial digestion with the PvuI.

EXAMPLES

Example 1

Sequence of BAV-1

By convention we will refer to the region containing the EcoR1 A fragment as the Left end of the BAV-1 genome. To complement the previously published restriction map (Maria Benko and B. Harrach, 1990 *Acta Veterinaria Hungarica* 38:281–284) other restriction enzyme sites in the BAV-1 genome were defined (PuvI, SmaI). The complete genome was cloned as several large restriction fragments. These included BamHI "B", "C", "D", "F", EcoR1 "A", "E", and PvuI "B". The genome was also clone in its entirety as described above (Construction of Recombinant BAV-1 Genomes in *E. coli*). These clones and 126 different oligonucleotide primers were used according to the method described above (DNA Sequencing) to determine an over lapping sequence for the entire BAV-1 genome.

This sequence (34,185 base pairs) contains 43 methionine initiated open reading frames (ORF) of greater than or equal to 110 amino acids (excluding smaller nested ORFs). All 43 ORFs were compared to the current version of the Genbank protein subset as described in the methods above (DNA Sequencing). Based on the BLAST analysis 28 of the ORFs (ORFS 1–28) exhibited significant homology to one or more other virus genes. Fifteen ORFs showed no significant homology to virus genes in the current version of Genbank (nORFs 1–15). Table 1 shows that the ORFs have a widely varying homology to adenovirus genes from several different species.

TABLE 1

BAV-1 Left end Open reading frames (Orf)

| ORF* | Location** | Best Match to GenBank*** | % Similarity. |
|---|---|---|---|
| ORF1 | 1400, 1867 | BAV-2 E1A | 49.5% |
| ORF2 | 2189, 2656 | BAV-2 E1B | 58.6% |
| ORF3 | 2566, 3777 | SAV-3 E1B | 42.3% |
| ORF4 | 3838, 4185 | BAV-2 Hexon | 36.9% |
| ORF5 RC | 4197, 5315 | HuAd-7 Maturation Protein | 69.6% |
| ORF6 RC | 5285, 8530 | BAV-2 Polymerase | 72.9% |
| ORF7 | 6255, 6680 | HuAd-7 unknown protein | 59.4% |
| ORF8 RC | 8527, 10185 | BAV-2 Terminal protein | 71.2% |
| ORF9 | 10376, 11437 | CAV-1 Orf9 | 63.0% |
| ORF10 | 11465, 13174 | CAV-2 Hexon protein | 57.0% |
| ORF11 | 13235, 14662 | SAV-3 Penton base protein | 74.6% |
| ORF12 | 14725, 15207 | BAV-2 Major core protein | 37.1% |
| ORF13 | 15267, 16388 | BAV-2 Minor core protein | 62.2% |
| ORF14 | 16703, 17113 | CAV-1 Minor capsid protein | 60.5% |
| ORF15 | 17509, 20238 | CAV-1 Hexon Late protein 2 | 75.3% |
| ORF16 | 20241, 20864 | BAV-2 endoprotease | 82.6% |
| ORF17 RC | 20906, 22246 | OvAV DNA binding protein | 77.8% |
| ORF18 | 22258, 24498 | BAV-3 Late 100 kd protein | 59.0% |
| ORF19 | 24212, 24796 | BAV-3 Late 33 kd protein | 44.0% |
| ORF20 | 25009, 25680 | BAV-1 Hexon protein | 97.8% |
| ORF21 | 25673, 26041 | BAV-1 E3 12.5 kd protein | 87.7% |
| ORF22 | 25923, 27287 | BAV-1 unknown protein | 85.8% |
| ORF23 | 27483, 29294 | HuAd-12 Fiber protein | 31.2% |
| ORF24 RC | 29311, 29730 | HuAd-40 E4 protein | 38.2% |
| ORF25 RC | 30404, 30739 | HuAd-12 unknown protein | 38.5% |
| ORF26 RC | 30730, 31464 | HuAd-40 E4 30 kd protein | 28.9% |
| ORF27 RC | 31471, 32232 | HuAd-9 E4 34 kd protein | 40.8% |
| ORF28 RC | 32956, 33384 | AvAd dUTPase | 54.7% |
| nOrf1 | 278, 736 | | |
| nOrf2 | 697, 1167 | | |
| nOrf3 | 5634, 5975 | | |
| nOrf4 RC | 10301, 10669 | | |
| nOrf5 RC | 12607, 13212 | | |
| nOrf6 RC | 14246, 14722 | | |
| nOrf7 RC | 15479, 16102 | | |
| nOrf8 RC | 17878, 18288 | | |
| nOrf9 | 19031, 19621 | | |
| nOrf10 | 21464, 21991 | | |
| nOrf11 RC | 24437, 24820 | | |
| nOrf12 RC | 27800, 28174 | | |
| nOrf13 RC | 29523, 30407 | | |
| nOrf14 RC | 32219, 32557 | | |
| nOrf15 RC | 33438, 33908 | | |

*RC, reverse compliment

**positions on SEQ ID NO: 3

***AvAd, Avian adenovirus; HuAD, Human Adenovirus; CAV, Canine Adenovirus, SAV, swine adenovirus; OvAd, sheep adenovirus SAV, swine adenovirus; OvAd, sheep adenovirus The E3 and E4 gene regions of BAV-1 can defined by homology to genes from the corresponding regions of the human adenoviruses. Evans et al (Virology 244:173–185) define the BAV-1 E3 gene region as bound by the TATA box sequence at positions 25362 to 25365 and the polyadenlyation signal at positions 27291 to 27296. Analysis of the gene homologies from Table 1 indicates that the E4 region of BAV-1 is bounded by the polyadenylation signal at positions 29059 to 29065 and the TATA box sequence at positions 34171 to 34174.

BAV-1 exhibits a complex sequence organization at its left and right ends. The genome exhibits an inverted terminal repeat (ITR) of 578 base pairs. A sequence of 419 base pairs is repeated twice at the left end of the genome. A single inverted copy of this repeat occurs at the right end of the genome. The two 419 base pair repeats a the left end of the genome are followed by a 424 bp sequence that appears as an inverted copy upstream of the 419 base pair sequence at the right end of the genome.

The sequence of the BAV-1 genome is useful for the construction of recombinant BAV-1 viral vectors. For example this information may be used by analogy to human adenovirus vector systems to predict non-essential regions that may be used as gene insertion sites. The information may also be used to predict intergenic regions, which may also be used as gene insertion sites.

Example 2
Method of constructing recombinant BAV-1 Viral Vectors

We have developed a novel procedure for the generation of recombinant bovine adenovirus vectors. This procedure takes advantage of recombinant viral genomes constructed as bacterial plasmids (see methods—Construction of Recombinant BAV-1 Genomes in *E. coli*). When DNA derived from these bacterial plasmids is transfected into the appropriate cells (see methods—Transfection of BAV-1 DNA) recombinant bovine adenovirus vectors are generated.

This procedure is exemplified by the infectivity of plasmid 990-50. DNA derived from this plasmid was transfected as described above into MDBK cells. Progeny viruses recovered from independent transfection stocks were amplified on MDBK cells and analyzed for growth characteristics, virus production yields, and DNA restriction patterns. In all cases, plasmid 990-50 derived adenovirus (S-BAV-002) was indistinguishable from wild-type BAV-1.

This procedure can be used to generate bovine adenovirus vectors expressing useful foreign DNA sequences. The procedure may also be used to delete genomic sequences from the bovine adenovirus vector. The production of bovine adenovirus vectors bearing a bovine diarrhea virus (BVDV) glycoprotein E2 (g53) expression cassette and deletions in E4 and E3 regions of BAV-1 respectively are described below (see examples 4–6).

Example 3
Preparation of Recombinant Adenovirus Vector S-BAV-003

S-BAV-003 is a BAV-1 virus that has a deletion in the E4 region of the genome. This deletion spans the EcoR1 H and G fragments. This deletion removes all or a major portion of ORFs 25–27 and nORF13. A poly linker sequence (GAATTCGAGCTCGCCCGGGCGAGCTCGAATTC) [SEQ ID NO: 15] containing a SmaI site was inserted into the deletion. As SmaI is absent from BAV-1 genomic DNA (see FIG. 1), the introduction of this poly linker sequence creates a useful unique SmaI site that may be exploited to directly engineer the virus.

S-BAV-003 was created by transfection of DNA derived from plasmid 1004-73.16.14 according to the method described above (Method of constructing recombinant BAV-1 viral vectors). The resulting viruses were purified according to the method above (Plaque Purification of Recombinant Constructs). Progeny viruses derived from independent transfection stocks were amplified on MDBK cells and analyzed for BamH1, EcoR1, and SmaI DNA restriction patterns. This analysis indicates that the EcoR1 G and H fragments have been deleted and a SmaI site has been introduced into the genome. S-BAV-003 was also shown to grow to similar titers as the wild type BAV-1.

Example 4

Preparation of Recombinant Adenovirus Vector S-BAV-004

S-BAV-004 is a BAV-1 virus that has a deletion in the E4 region of the genome. This deletion spans the EcoR1 H and G fragments. This deletion removes all or a major portion of ORFs 25–27 and nORF13. The gene for the bovine viral diarrhea virus (BVDV) glycoprotein 53 (g53) (amino acids 1–394) under the control of the HCMV immediate early promoter was inserted into the deleted region.

S-BAV-004 was created by transfection of DNA derived from plasmid 1004-40 according to the method described above (Method of constructing recombinant BAV-1 viral vectors). The resulting viruses were purified according to the method above (Plaque Purification of Recombinant Constructs).

Example 5

Preparation of Recombinant Adenovirus Vector S-BAV-005

S-BAV-005 is a BAV-1 virus that has a deletion in the E3 region of the genome. The smaller SalI to BamH1 sub fragment of BamH1 fragment "B" (positions 25664 to 26850 from SEQ ID NO: 3) has been deleted. This deletion removes a major portion of ORFs 21 and 22. A poly linker sequence (5'-TCGACAAGCTTCCC-3') [SEQ ID NO: 16] containing a HindIII site was inserted into the deletion.

S-BAV-005 was created by transfection of DNA derived from plasmid 1018-75 according to the method described above (Method of constructing recombinant BAV-1 viral vectors). The resulting viruses were purified according to the method above (Plaque Purification of Recombinant Constructs).

Example 6

Preparation of Recombinant Adenovirus Vector S-BAV-006

S-BAV-006 is a BAV-1 virus that has a deletion in the E3 region of the genome. The smaller SalI to BamH1 sub fragment of BamH1 fragment B (positions 25664 to 26850 from SEQ ID NO: 3) has been deleted. This deletion removes a major portion of ORFs 21 and 22. The gene for the BVDV g53 (amino acids 1–394) under the control of the HCMV immediate early promoter was inserted into the deleted region.

S-BAV-006 was created by transfection of DNA derived from plasmid 1018-42 according to the method described above (Method of constructing recombinant BAV-1 viral vectors). The resulting viruses were purified according to the method above (Plaque Purification of Recombinant Constructs).

Example 7

Preparation of Recombinant Adenovirus Vector S-BAV-007

S-BAV-005 is a BAV-1 virus that has a deletion in the E3 region of the genome. The smaller EcoR1 to BamH1 sub fragment of BamH1 fragment "B" (positions 25765 to 26850 from SEQ ID NO: 3) has been deleted. This deletion removes a major portion of ORFs 21 and 22. A poly linker sequence (5'-TCGACAAGCTTCCC-3') [SEQ ID NO:16] containing a HindIII site was inserted into the deletion.

S-BAV-007 was created by transfection of DNA derived from plasmid 1018-45 according to the method described above (Method of constructing recombinant BAV-1 viral vectors). The resulting viruses were purified according to the method above (Plaque Purification of Recombinant Constructs). Progeny viruses derived from independent transfection stocks were amplified on MDBK cells and analyzed for BamH1, EcoR1, and XbaI DNA restriction patterns. S-BAV-007 was also shown to grow to similar titers as the wild type BAV-1.

Example 8

Preparation of Recombinant Adenovirus Vector S-BAV-014

S-BAV-014 is a BAV-1 virus that has a deletion in the E3 region of the genome. The smaller EcolR1 to BamH1 sub fragment of BamH1 fragment B (positions 25765 to 26850 from SEQ ID NO: 3) has been deleted. This deletion removes a major portion of ORFs 21 and 22. The gene for the BVDV g53 (amino acids 1–394) under the control of the HCMV immediate early promoter was inserted into the deleted region.

S-BAV-014 was created by transfection of DNA derived from plasmid 1038-16 according to the method described above (Method of constructing recombinant BAV-1 viral vectors). The resulting viruses were purified according to the method above (Plaque Purification of Recombinant Constructs). Expression of the BVDV g53 gene was assayed by the Western Blotting Procedure. S-BAV-014 exhibited expression of a correct size protein with specific reactivity to BVDV g53 antibody.

Example 9
Preparation of Recombinant Adenovirus Vector S-BAV-022

S-BAV-022 is a BAV-1 virus that has a deletion in the E4 region of the genome. This deletion spans from positions 29523–30407 of SEQ ID NO: 3. A linker sequence 5'-CTGCAG-3' containing a PstI site was inserted into the deletion.

S-BAV-022 was created by transfection of DNA derived from plasmid 1055-52 according to the method described above (Method of constructing recombinant BAV-1 viral vectors). The resulting viruses were purified according to the method above (Plaque Purification of Recombinant Constructs). Progeny viruses derived from independent transfection stocks were amplified on MDBK cells and analyzed for BamH1, EcoR1, and XbaI DNA restriction patterns. S-BAV-022 was also shown to grow to similar titers as the wild type BAV-1.

Example 10
Preparation of Recombinant Adenovirus Vector S-BAV-023

S-BAV-023 is a BAV-1 virus that has a deletion in the E4 region of the genome. This deletion spans from positions 29523–30407 of SEQ ID NO: 3. The gene for the BVDV g53 (amino acids 1–394) was inserted into the deleted region. The BVDV g53 gene was under the control of E4 promoter(s).

S-BAV-023 was created by transfection of DNA derived from plasmid 1055-56 according to the method described above (Method of constructing recombinant BAV-1 viral vectors). The resulting viruses were purified according to the method above (Plaque Purification of Recombinant Constructs). Expression of the BVDV g53 gene was assayed by the Western Blotting Procedure. S-BAV-006 exhibited expression of a correct size protein with specific reactivity to BVDV g53 antibody. Expression of the BDV g53 foreign antigen in S-BAV-023 establishes the utility of the BAV-1 E4 region promoter for transcription of foreign genes in vector systems.

Example 11
Preparation of Recombinant Adenovirus Vector S-BAV-025

S-BAV-025 is a BAV-1 virus that has a deletion in the E4 region of the genome. This deletion spans from positions 33614–33725 of SEQ. ID NO: 3. A linker sequence 5'-CTGCAG-3' containing a PstI site was inserted into the deletion.

S-BAV-025 was created by transfection of DNA derived from plasmid 1064-26 according to the method described above (Method of constructing recombinant BAV-1 viral vectors). The resulting viruses were purified according to the method above (Plaque Purification of Recombinant Constructs). Progeny viruses derived from independent transfection stocks were amplified on MDBK cells and analyzed for BamH1, EcoR1, and PstlI DNA restriction patterns. S-BAV-025 was also shown to grow to similar titers as the wild type BAV-1.

Example 12
Preparation of Recombinant Adenovirus Vector S-BAV-026

S-BAV-026 is a BAV-1 virus that has a deletion in the E4 region of the genome. This deletion spans from positions 29523–30403 of SEQ ID NO: 3. A linker sequence 5'-CTGCAG-3' containing a PstI site was inserted into the deletion.

S-BAV-026 was created by transfection of DNA derived from plasmid 1066-44 according to the method described above (Method of constructing recombinant BAV-1 viral vectors). The resulting viruses were purified according to the method above (Plaque Purification of Recombinant Constructs). Progeny viruses derived from independent transfection stocks were amplified on MDBK cells and analyzed for BamH1, EcoR1, and XbaI DNA restriction patterns. S-BAV-026 was also shown to grow to similar titers as the wild type BAV-1.

Example 13
Preparation of Recombinant Adenovirus Vector S-BAV-027

S-BAV-027 is a BAV-1 virus that has a deletion in the E4 region of the genome. This deletion spans from positions 29523–30403 of SEQ ID NO: 3. The gene for the BVDV g53 (amino acids 1–394) was inserted into the deleted region. The BVDV g53 gene was under the control of E4 promoter(s).

S-BAV-027 was created by transfection of DNA derived from plasmid 1066-51 according to the method described above (Method of constructing recombinant BAV-1 viral vectors). The resulting viruses were purified according to the method above (Plaque Purification of Recombinant Constructs).

Example 14
Shipping Fever Vaccine

Shipping fever or bovine respiratory disease (BRD) complex is manifested as a result of a combination of infectious diseases of cattle and additional stress related factors (C. A. Hjerpe, The Bovine Respiratory Disease Complex. In: Current Veterinary Therapy 2: Food Animal Practice. Ed. by J. L. Howard, Philadelphia, W. B. Saunders Co., 1986, pp 670–680.). Respiratory virus infections, augmented by pathophysiological effects of stress, alter the susceptibility of cattle to Pasteurella organisms that are normally present in the upper respiratory tract by a number of mechanisms. Control of the viral infections that initiate BRD as well as control of the terminal bacterial pneumonia is essential to preventing the disease syndrome (F. Fenner, et al., "Mechanisms of Disease Production: Acute Infections", Veterinary Virology. Academic Press, Inc., Orlando, Fla., 1987, pp 183–202.).

The major infectious diseases that contribute to BRD are: infectious bovine rhinotracheitis virus, parainfluenza type 3 virus, bovine viral diarrhea virus, bovine respiratory syncytial virus, and *Pasteurella haemolytica* (F. Fenner, et al., "Mechanisms of Disease Production: Acute Infections", Veterinary Virology. Academic Press, Inc., Orlando, Fla., 1987, pp 183-202.). An extension of this approach is to combine vaccines in a manner so as to control the array of disease pathogens with a single immunization. To this end, mixing of the various BAV-1 vectored antigens (IBR, BRSV, PI-3, BVDV and *P. Haemolytica*) in a single vaccine dose. Also, conventionally derived vaccines (killed virus, inactivated bacterins and modified live viruses) could be included as part of the BRD vaccine formulation should such vaccine components prove to be more effective.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A recombinant virus comprising a foreign DNA sequence inserted into the region encoding the E4 gene of a bovine adenovirus.

2. The recombinant virus of claim 1, wherein said foreign DNA encodes a polypeptide from a virus or bacteria selected from the group consisting of bovine rotavirus, bovine coronavirus, bovine herpes virus type 1, bovine respiratory syncytial virus, bovine para influenza virus type 3 (BPI-3), bovine diarrhea virus, bovine rhinotracheitis virus, bovine parainfluenza type 3 virus, *Pasteurella haemolytica, Pasteurella multocida* and/or *Haemophilus somnus*.

3. The recombinant virus of claim 2, wherein said polypeptide comprises more than ten amino acids.

4. The recombinant virus of claim 2, wherein said polypeptide is antigenic.

5. The recombinant virus of claim 1, wherein said bovine adenovirus is a Subgroup 1 bovine adenovirus.

6. The recombinant virus of claim 5, wherein said foreign DNA sequence is under control of a promoter located upstream of said foreign DNA sequence.

7. A vaccine comprising the recombinant virus of claim 1.

* * * * *

SEQUENCE LISTING

<160> NUMBER OF SEQ ID NOS: 17

<210> SEQ ID NO 1
<211> LENGTH: 42
<212> TYPE: DNA
<213> ORGANISM: Artificial Sequence
<220> FEATURE:
<223> OTHER INFORMATION: Description of Artificial Sequence: DNA Primer

<400> SEQUENCE: 1
cttggatcct catccatact gagtccctga ggccttctgt tc            42

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence: DNA Primer

<400> SEQUENCE: 2
catagatctt gtggtgctgt ccgacttcgc a               31

<210> SEQ ID NO 3
<211> LENGTH: 34185
<212> TYPE: DNA
<213> ORGANISM: Bovine adenovirus type 1

<400> SEQUENCE: 3

| | | | | |
|---|---|---|---|---|
| catcatcaat | aatatacgga | acacttttgc | gtgatgacgt | tgacgtgctg | tgcgtaaggg | 60 |
| ggcgtgggaa | aattgttcaa | aggtcgctgg | gcgggagttt | ctgggagggg | cggggagtgt | 120 |
| ccgtgtgcgt | gcgagcggcg | gggcgaggcg | ctgagtcagg | tgtatttatg | atggggtgtt | 180 |
| tagggtatca | gctgttggac | tttgactttc | actgtcgtaa | atttgccact | ttattggagc | 240 |
| cctttgcccg | cggacgtgga | gggatttttc | ccaatttatg | gccactttta | ctgcgatgcc | 300 |
| gcacgaaacc | tgtctaaagg | tctatgccac | gtctcccatc | atgggcggtc | ttttttctct | 360 |
| atgcaccact | cccagtgagc | tatatattac | ctgcgcaggt | aaagaggtgc | cactcttgac | 420 |
| atcatcaata | atatacggaa | cacttttgcg | tgatgacgtt | gacgtgctgt | gcgtaagggg | 480 |
| gcgtgggaaa | attgttcaaa | ggtcgctggg | cgggagtttc | tgggaggggc | gggagtgtc | 540 |
| cgtgtgcgtg | cgagcggcgg | ggcgaggcgc | tgagtcaggt | gtatttatga | tggggtgttt | 600 |
| agggtatcag | ctgttggact | ttgactttca | ctgtcgtaaa | tttgccactt | tattggagcc | 660 |
| ctttgcccgc | ggacgtggag | ggattttttcc | caatttatgg | ccacttttac | tgcgatgccg | 720 |
| cacgaaacct | gtctaaaggt | ctatgccacg | tctcccatca | tgggcggtct | tttttctcta | 780 |
| tgcaccactc | ccagtgagct | atatattacc | tgcgcaggta | aagaggtgcc | actcttgaca | 840 |
| tcatcaataa | tatacggaac | acttttgcgt | gatgacgttg | acgtgctgtg | cgtaaggggg | 900 |
| cgtgggaaaa | ttgttcaaag | gtcgctgggc | gggagtttct | gggagggggcg | ggagtgtcc | 960 |
| gtgtgcgtgc | gagcggcggg | gcgaggcgct | gagtcactgc | ccttttgcac | tgtcttgtgc | 1020 |
| tttgtcacgc | ggtttcggtt | acgcctgtca | ggcgccagaa | gcccttttcgc | ctcgtcacag | 1080 |
| accgcgcctt | ttcgctctat | aaagccattt | ctctcctctg | ctcgtcattc | gcctctgctc | 1140 |
| ctgagccttc | tgtgctgcca | tttctaaact | tacactcctt | gctgtaggcc | gtggtctact | 1200 |
| ttgccaagag | taagtacatc | atggctgaca | agctgctctt | tgtgcgtgtg | tctgactcgg | 1260 |
| cttgccacgt | ctcccatcat | gggcggtctt | ttttctctat | gcaccactcc | cagtgagcta | 1320 |

-continued

```
tatattaccct gcgcaggtaa agaggtgcca ctcttgagtc gaagagagta gagttttctc   1380
atctgctcat tcattcacca tgaggcacct aagactcgct tttgatgagc gcttctggat   1440
agccgccgaa ggtttgctgg cggattctcc tgctgatgaa gatgagggat ttcatgagcc   1500
tttgtctttg caggacttga ttgaaattga tgacgcttca gacgtggtta gcttatttt   1560 ccctgaactt gaagttcagc aagacctgcc aacagcggga gaggttgagg acttgttaca   1620
ctgtgaggag actgctgctg acttagaatc tgtttctgac ttaccgcctg tggagtctcc   1680
tgaacctccg gattctcact tttccacatt tgagttggat tatcctgaga tacccggcgt   1740
gaattgctct gcatgctcat tcatcgtca ggagactgga tctgaggagg ctgtatgctc    1800
gctctgctat atgagaaaaa cggcttatgc tgtatatggt aggttgcttt acatactttt   1860
cttttgatta ctcttgcatt gcaatattag cctaatgtgt tgatttgtgc ttgcagagcc   1920
tgtttctcca gctccgccta ctgttgatga gcaaacatgag acaggtgcgc cagtttcgtc   1980
tccgcctgct ggccgcaagc ggcgccacca ggatgacctc atactgttta accataaacg   2040
ctgcgcccag gatgaacctt tggacttgtc cttacccaag cccaatgccc aataaactat   2100
gttaatcagt acctagaaag gtgtggtcac tgcctatata aactagggag cgctgctcag   2160
atgcagcctg gcgctcactt ggactaccat ggacatttct ctgggctttt gcgaaaagct   2220
gtccgatttc caatacttaa gacgggtgct gtactacgcc tcagccagac caggttggtg   2280
gacacgcact ctctgtgggg acagactctc aagtttggtt tataatacaa aaattgagca   2340
ttggaaaaac ttagaggaaa tttttaaacg cgattcaggt ttctggtcta tgctttctag   2400
tgggcgcagc cttgggtttg aggcgaaagt agttccttgg ctggatttt cgtctccagg    2460 gagaactgtg gccagtttat cgttactaac ttatattgtt gatactttgg ataaacagac   2520
tcagctgagc ccagattaca ttttggactc gatttgcggc ccagtatgtt tcaggctgaa   2580
aaccttggtt tcaatcagga aaatgcagca agccgtgcgg ggtcaggagg gtccaattat   2640
agaggaagtg gattaaaccc agacggtata ccataccagt ctatattgat ggagtttgct   2700
agagatccat tttctactca tgacaaatat gattttgaga cagttcagac ttactttctt   2760
aagccagggg atgatttaga aacagtgatc agccagcatg ctaaaattgc tttagatcct   2820
gaggtagagt atgtgattga acatccagta aagattcgat ctctgtgtta tataattggc   2880
aatggagcta aaataaaaat agcatgtcca gaacactttg gaatagaaat ttatccaaga   2940
gatcacagcc ctggtatagt tggaatgtgg cttgtcacat ttaacaatgt ggtgtttgaa   3000
agggaacgaa gtattcctgg tggcattatt cagagtagga cattcttttt gtgccatggc   3060
tgtaatttct tgggagcatt gggaacagct gtttcggctc tggctggtgg ggaagttagg   3120
gggtgccatt tctttggatg tttcaagtgt gttgatagta aagtaaatt taaggtgaaa    3180 gttagccact ctgtaattga gacttgtatg gtaggcataa gcgcttcagg gccagtgagt   3240
gtaaagcatt gtcaaggatt gagtgtgtac tgctttttgt ttatgttagg agctggtaag   3300
gttgagggaa acagtgtgat caacccaaac aagttttatg agtctgccct tacagagatg   3360
gtgtcttgct atggcaaaat tgttttgccc ctggccactg ttcatatttc ggcctcgccg   3420
aaacatcagt atccacactt tgaagcaaat gtgctgacaa gatgtaaggt gtttgtgggc   3480
gccaggcaag gcacttttac gccaatgctt tcatcactaa gttatacttc tattgtggct   3540
gaccgcgatg ctttcaaaag cctgaatctg aattatactt tcaccaaaac tactactatt   3600
tggaagcttc tgagtgctgc tgatgctgac tttgaccatg gaactgccag aaagtgcctg   3660
```

```
tgtggtgatt tgcatccatg tcctgtgttg aagcagcttg attacacaag ccgggttagg    3720
cctaacccat acgaccactc atgtgattcc agggtgtttt ctgatgacga gaattaaggt    3780
aagccacgcc caccatctat ataagcggga gtaaaagcgt ggggtggtat ttgcacaatg    3840
actgatcaag gtgacattcg tacgtgtttt cttacagcga gactgcccag gtgggcaggt    3900
gttcgccaaa atgtcgtcgg gtcaaatatt tctggtggcg ttgtcgactc cccggagacg    3960
cttctggcat ctagatctaa cgcggcagct gcgatgatga ctttgaggaa catcgcgacc    4020
agcagacagt tggaagagca ggtggagact tgctggagc agaacttgga tctgacggcc    4080
cagcttaatg ccttgctgat gcgtgtcaac gcgattgaac ggcagctagc tgatatgcag    4140
cgcgacttgg aaccaatcat tcaacaacac aatgcaataa tttgatcaat aaatctttat    4200
ttctttgcat gataatatcg agtccagcgt tgtctgtcag caattacttt gctaattttt    4260
tccaaaatag agtacagttt acattgcaca tttagataca ttggtataag tccttctgat    4320
gggtgtaggt atgaccactg tagggcttca ttttctggac atgtattata aattatccag    4380
tcatagttgg tgttaatttt gtgatagttg aatatgtctt ttagcaggag ggaaattggc    4440
aatggcagtc ctttagtgta ttgatttata aatctattaa gctgtgaagg ctgcattta    4500 ggagagatga tgtgcagctt tgcttgtatt ttaaatttg atatgttccc agcgtgatct    4560 tttctgggt tcatattgtg caatactacc atgacagagt agcctgtgca ttttggaaac    4620
ttatcatgta gtttagatgg aaatgcgtgg aaaaactttg aaattccttt gtgggctccc    4680
agatcctcca tacattcgtc tagtattata gcgattggac ctttgatgc cgctttagca    4740 aatatgtttc tggggtcgct caggtcatag ttgtattcct gcgttaggtc tgaatatgcc    4800
atttttatga atttggcat cagcgagcca ctctgtggaa ctaaggtccc ctgaggcccc    4860
atgctgtagt tgccttcaca gatctgtgtt tcccaagcac ttatctcttg gggggtatc    4920 atgtcaattt gcggcactat aaagaaaaca gtttctgggg gcgtgtgat taactgtgag    4980 gaaattatgt tcctaagaag ttgggatttg ccgcagcctg tggggccgta acaacccct    5040 atgacaggct gcatctgaaa attaatagac ctgcatgccc cttgcgggtt caaataaggt    5100
acgcatttat taagcaactc cctgacacaa acatttctct cagccaaatc taaaagtaaa    5160
ctgtgtccgg ctaatgacat cagttgctgg aagaggaga acgtgtgaag aggttttagg    5220
ccttcagcaa aaggcatgct ttttaagctg ttgtgcaaga cggtcagtct gtcccatagt    5280
tcatttatat gtcccacggt aatgtcatcc agcatttgtc gccgtttctt ggatttgggt    5340
tgcttttgga gtagggcatt agtcgatgct ggtcgaggtt tacgagggtt ctgtccttcc    5400
acggcctcac tgtccgagtc agagttgtct ctgtcactgt gaatggagcg gcgtttgctt    5460
ggtttgtcgc tagagtgcgc ttcaggctca tccggctggt ctgaaagtgg tctgagccgt    5520
gctggctgtc cgctaggtag cactgggcga gagtatcata agatagctca gtggttgcgt    5580
gccctttagc tcttagcttg ccttttccca cgtgaccgca gttagggcag tgtatgcttt    5640
tcaacgcata cagctttggc gccaggaata cagattcagg actgtatgca tcactcttgc    5700 attttcgca ctgcgtttcg cattctacta gccaggtgat gcttgggcag cttgggtcaa    5760
acactagact tcctccattt tttttaattc tatgtttacc tttttcttgc attaggcgat    5820
gtccttcttc tgtcacgaac aggctgtcgg tgtcaccgta cacggacttg attgtgcgtt    5880
gttccatggg ctttcccctg tcgtcgctga caggaactc ggcccactcc gccacaaaca    5940
ctcttgtcca agctagcaca aaagaagcga tgtgagaagc gtaccggttg ttttttgataa    6000 gtaaagaatt tgctcgagg gtgtgtaaac aaatgtcatc gtcatcggtg tccatgaatg    6060
```

-continued

```
tgattggctt gtaagtgtag gtcacgtgac ccgccgtagg tataaaaggg gcggggtcct    6120
cgtcttcctc atttgcttct ggctcgacgt gcggtgcagg tgggtaggct acggtaaatt    6180
ctggcataag ttcagcactt aagttgtcgg tttcaatgaa agaagaggat ttgacactgt    6240
aggtgccagt ggcgatgttt tttgacattt ctgattcaag ctggtcagaa aacactattt    6300
ttttgttatc gagtttagta gcaaagctgc cgtacagagc atttgacaac agtttggcta    6360
tgctgcgcat tgtttggttt ttgttttttgt ctgcttttc tttggcggct atgttcagct    6420
ggacatattc tttagccacg caacgccatt ctggaaatat tgttgttctt tcatctggta    6480
gtatgcgcac tttccagcct ctgttgtgca gggttatcat gtctactgat gtggcaacct    6540
caccgcggag aggctcgttt gtccagcata gcctgcctcc cttcctggag cagaagggcg    6600
ggagctcgtc caggaagagt tcgtctggag ggtcggcgtc cactgtgaag atacctggca    6660
acagcgtgtc atcgaaataa tcaatgcgcg aaccatgcgc gctcaacctt ctgctccagt    6720
ctgatgcagc aactgcgcgc tcgaatgggt tcagcggctg ccccgctgga aatggatgag    6780
tcaatgcgct tgcatacatt ccacagatgt catacacata aataggctgt tccagtatgc    6840
cgatgtatgt ggggtagcag cgtcccccac ggatgctttg gcgaacgtaa tcatacatct    6900
cgtttgacgg cgcaagcagg gtgtttgaca tgttggaacg gttaggtttg attgagcgat    6960
acaaaatttg tttgaagatt gcatgggagt ttgagctaat tgttggtctt tgaaaaatgt    7020
tgaatgctgc ttcaggtaag tcaacttctt tctgaatgaa ctgctggtat gagttttgga    7080
gttttctgac cagctcagag gtgactaaaa catcttgggc gcaatattca agcgtttgct    7140
ggatgatatc gtaagccccc acgttttttt ctctccacag cgctttgttg agctcgtatt    7200
ctgctgtgtc cttccagtac cgaaggtgtg ggaaaccatc ctcgtcctgc tggtaagagc    7260
ccaggcgata aaattcgttt accgcttcgt acggacagct tcccttttct actggaagtt    7320
catacgccga tgcggcattt ttcaagcttg tgtgtgtcaa cgcaaatgtg tctctgacca    7380
tgaacttaac gaactgcatt ttgtagtctc ctgctgtcat ttttcccagt tcccagtcct    7440
caaatgtttt cctggaaaca acttttgggt ttggaagtcc aaatgtgatg tcattaaata    7500
aaatctttcc atttcttggc ataaagtttc tacttatttt aaatgctgga aggacctcat    7560
ctctgttgtg aatcacttga gccgccagca cgatttcatc gaaaccgcag atgttatgtc    7620
ccaccacata tatttccata aacttagggt ctccgtttag ttgacacttt ctaagcatct    7680
caaatgtgat atcatctact gcagctaggc catgttgctc tttaagctgt tccagatgtg    7740
ggttgtgagc gagaaggtgc tcccatagta tggcggtcgt gcgccgctgt acggcgtcgc    7800 ggaactttttt aaaagctctt cccacctctc cctttgttgg ggtgatgata tagtaagtgt    7860
acttttcgcg ccacgctgtc cactctaggt ttatggcgac attattcgcg gcttctagca    7920
gctcgctgtc cccagatagg tgcatcacta gcataaatgg caccagttgt ttgccaaagc    7980
gcccgtgcca ggtgtaagtc tccacgtcgt atgtgatgaa cagcctttga atgtcaacgt    8040
acgagcctat tggctgaaat gggataagtt cccaccagtc ggcagattta tgattgacgt    8100
ggtgaaagta aaaatcacgc ctccgcacag aacaagtgtg agaatgtttg taaaagtctc    8160
cacagaaatc acattttgc gagggtgaaa tttcttttat taaaaacacc ttcccatgtt    8220
tgacgaagaa attaattgaa aaaggtagga tgctttcttc catgattgtg gactttttg    8280 aaattcttcc tttgttgtag ataaaaacac ctccgtcact cggtagtagg ctttctaaca    8340
ttgcgagggc gtttcgtgga gtgaccgctg cggcgttaaa gtgatcaggc atgtcaaata    8400
```

```
gatgaatgtg gaaaaggttt gcaagtgctg gctgtagtgc gctgtggtat ttgatttcga    8460
cgtgggtccc atcctccatt gtcccactgc ttgttagcgt ggcgcgtttg gccactactg    8520
tgcctctcat tgctcttccg gcggcggaag gcgcactgct tcgtttagcg ccggcagtgg    8580
acgccgttct tgacgcaaca ttgttgctgc gcgtatcact cgtcggttta tattctggat    8640
ttccctcagg ccggagaaca ccacaggacc gctcactcga aacctgaaag atatttcgat    8700
agaatcaatt tcagaatcat tggtggccac ctgtcttaga atttctgtta catcgccgct    8760
gttttcgtga tatgctatttt ctgccataaa ttgttctatt tcctcctcct cgagctctcc   8820
tctgccagcg cgctcaacgg tggctgccaa atcaacactt attctgttca taatagcaga    8880
aaacgcttgc tcgccgtttt cgttccagac gcgactgtag accagcctgc cgtcctgaga    8940
ccttgctctc atgaccactt gtgccagatt tagcatgacg tatcttccga atgggctcgc    9000
gactctcagt tgatgattta agtagttgag agtggtggcg atgtgctccg ccacgaagaa    9060
atacatcacc catcgcctga gtgtcagctc gttgatatcc ccaagcgctt ctaaacgctg    9120
tataacttcg tagaagttca cagcaaaact gaaaaactgc tgatttctgg ccgcaaccgt    9180
cagctcttct tcaagcaatc tgattgcttc agccactgcc gctctaactt cttcttcaaa    9240
cgtagtctca gggctttctt cctcaacttc cattggcgcc tcttccggtg gtggaggcgg    9300
ctgtcttcgg cgccgtctgc gcatcggaag acggtccacg aactgttcta tcatttctcc    9360
tctggctctt ctcatgcttt ctgtgactgc ccggtttcct tctcttggtc gtagctggaa    9420
agcgcctcca ctcatggctg tgccgtggca actgggggagg ctcagtgcgc taataataca   9480
ttttgtcaat atttgcgcag gaacttgttg cagcctcatt gcttcgctga tatcggcaga    9540
ttgatcgctt tcggcgaact tctccacgaa ggcatttaac caatagcagt cgcaaggtaa    9600
gtttaactct tgctcttggg ctagtgggag gtggcggcat attagaaagt tgaaatatgc    9660
tgttttgagc ttgcgaatcg atgacagcac cactaagtct tgcgcccgg cgttttgcac     9720
tctgattctg tcagccagcc cccaggcttg gccctggcat gcccctatgt ccttgtattg    9780
ttcctggagc aagtattcca cgggaacgtc gtttctatcg actgaggtgc gaccaaatcc    9840
ccgcattggt cggataagag ctaggtctgc tacgatgcgc tctgccagaa tagcctgctg    9900
gacggctgtg agcgtttcag aaaagttgtc catgtctatg aagcgatggt atgccccggt    9960
gttcacagtg tatgagcagt ttgccattac tgaccaattc attatctgcg atccaaagct   10020
aagctgttcg gtgtattta accggctgta tgctctggcg tcaaaaatgt agtcgttgca    10080
tatctgcaac agcttttgat atccaaccaa aaagtgcggc ggtgggtagt tatataacgg   10140
ccagttccta gtagccggct cccgcggcga tagattcatc agcattaggc ggtgatattg   10200
gtagacgtgt cttgacagcc atccgagccc ggctggtgtg acagcagccc ttgcccaatc   10260
ttggacacgt ttccaaatgt tgcgcactgg cctaaacact tcaattgtgt aaacgctctg   10320
gccggtcagg cgcgcgcagt cgatggcgtt ctaaaagaaa taaacaacat gtccaatggg   10380
atttgtgcag atgcatccgg tgctgcgcca gctgaaacca ttgccccata gtaaggcatc   10440
gcccgttgta acgtgggccg atgacgaccc cgcgcctacg ccgcccatcc aggagggaga   10500
gggtgttgcg cgactgaacg tggagagccc cgagcaacac cccgtgttc agcttaagaa    10560
ggatgccgga gaggctttcg tcccacccgc caatgtattc agagaccggg agggcgaaga   10620
ggaggctcag atgaggcaca tgagatttaa agcgggagaa caaatgcatg tccctaagaa   10680
gcgcgtgcta agtgatactg actttgaagt ggatgaggtg tccggggtga gcccagccaa   10740
ggctcatatg gcggcagccg atctgctgac cgcctatcag caaactgtca gagaggaggt   10800
```

```
caacttccaa aagacattta ataataatgt tcgaacactg gtggccaggg aagaagtggc    10860
agtggggctc atgcatttgt gggactttgt tgaggcgtac gttgtaaatc catcttccaa    10920
agctttaact gcccagctat ttcttattgt ccaacactgc cgcgacgaag gcattctaaa    10980
ggaatcgctg ttgaacattg cagagccaga gagcaggtgg ctgttagatc taataaatct    11040
gctccaaacg atagtggttc aagaacgggg catgtccatt acagaaaagg tggccgccat    11100
taactattct gtaataactc tcagcaagca ttatgccagg aaagtttata ggactccgtt    11160
tgtccccatt gacaaggaag caaagatcac cacttttttac atgcgaattg tggttaaact    11220
gttggtgttg agcgatgact tgggcatgta tcgtaatgag cgcatggagc gggtagtcag    11280
cgctgcccgc agacgagaat tcacagataa agagctgatg ttcagtttgc gtaaagcgct    11340
ggcaggagaa gacgaggtat atgacggcca attagaatct gctgttcaga gcgtgccagg    11400
tatagaatgg gcgcatgagg atgatgacga cgagtagtaa gatgttatct tggttacagc    11460
cgccatgttt cgctcccgca acaccgtgtc tgcggcgcgc aatcctaacg ccttggcgcg    11520
cctgcagtct caagcgtctg gggacgtgga atgggccgat gccattaagc gtataatggc    11580
tttgaccgcc agatacccgg aagcgttcgc tagtcagcca tttgcaaata ggatcagcgc    11640
tattcttgag gcggtggttc cttctagaaa aaatccgact catgaaaaag tgctgtcaat    11700
tgtcaacgcc ttggtagaaa cgggcgctat tcgtcctgat gagggagggc aggtgtacaa    11760
cgctctgctt gagagggtat ctcgatacaa cagtatgaat gttcagacta gtatagacag    11820
gcttagtcaa gatgtgagaa acgtagttgc tcaaaaggaa aggatggttg gagagaacat    11880
ggggtcgatg gtgcccctta atgcatttttt gtcaactctg ccggccaatg tggagagagg    11940
gcaggaaaat tacacagctt tcataagcgc tttgaggctg ttggtgtctg aagtgcctca    12000
gactgaagta tatcagtctg ggccaaatta ctacctgcag acctctagga atggcagtca    12060
cactgtcaac ctgactagag cttttgaaaa cctgagctct ttgtggggag tgaatgcgcc    12120
agtggccgaa cgaagtgcca tatcttccat tctcactcca aacactaggc tgctgcttct    12180
gcttatagcc ccgtttacag acggggttaa catttccaga gcttcataca ttggttacct    12240
gctgacccta tacagggaaa ctatcgggca ggctcatatt gacgaaagaa catacaatga    12300
gattactagc gtaagccggg ctgttggcaa cgaagacgct gcaaacctgc aggccacatt    12360
gaatttccta ctgacaaatc ggcagtacag gatccctaaa gagtactcat tgacgccaga    12420
ggaggagcga atattacgtt ttgtgcagca gtctgtcagc ctgcatatga tgcaagacgg    12480
cagcacacct tctgccgccc ttgatgaaac aagccgtaat tttgaaccta gcttttatgc    12540
gggaaatagg ttattcatta acaagctgat ggattatttt cacagggctg ccgctgtagc    12600
cccaaactat tttatgaacg cggttctaaa tccaaaatgg ctccctcctg aagggttttt    12660
tactggcgtc tttgattttc ctgagggcga tgacggtttt gtgtgggacg atacagatgt    12720
atctgaggtt ggggcgagag gtgccgttcc ggcgctagtg gccaagaaag agggagggga    12780
tgattcagat ctgtccatca cgatcccctc tattcccagg cagttacgca gggcttctgt    12840
tgtgtctgat actagcgaca tgagccgcgg tagggtgcgc agccgcagtc gtgtacgacg    12900
gccggtagac atagacattg ggcgctggct agaggacaaa aacactaatg cgacccgagc    12960
ctcagctgct attaataacg aaatggaaaa tttagtcgac aagatgacta atggcgcac     13020 gtatgcccag gagcaaatgg aggaagtcag agcgcgctct cccataaaaa tagaacagga    13080
tgatgatgat tggagaaacg acaggttttt gaagtttgaa ggcagtgggg cagtcaatct    13140
```

-continued

```
gttcagccac ttaaagccaa aaggcatggt gtaacaaaaa aaaaaaaaaa taaagtcact    13200
taccacagac atggtttggt tttgtgattg ctagatgata cgagccaggc cagtggaatc    13260
gcctcctcct tcctatgaga gcgtggtcgg cactatggat ccgctctacg tgccccgcg     13320 atacttgggt cctactgaag gaagaagcag catccgttac tccctattgc ccccgcttta    13380
tgacaccacc aagctttact ttatcgataa caagtcggca gatatttcgt cactcaatta    13440
tcaaaataac cacagcaatt acctcaccag tgttgtgcaa aacagcgact acacgccgca    13500
ggaggctagc acgcaaacta taaactttga tgataggtcg cggtgggggg cggactttaa    13560
aactattttg catatgaaca tgcccaacgt gactgaattt atgtttagca attcattcag    13620
ggctaaattg atgtctgcca aggtgggtgg caacccaacc tatgagtggt tcactctcac    13680
cattccagag ggcaactact cagacattgc agtcttagac ttgatgaata atgcgatagt    13740
agaaaattat ctgcaggttg gacgccagaa tggagtagcg gaagaagaca taggcgtaaa    13800
gtttgacact agaaatttca gattgggcta tgatcctgta acccagcttg taatgccagg    13860
gaaatatact tatttggctt ttcacccaga catcatactc gcccctggct gtgcggtaga    13920
ctttacaacg agccgcctaa acaatctact tggtattcga aaaaggcagc catttcagga    13980
aggatttcaa atagcctatg aagatttggt aggtggtaat attccagctc tccttgacgt    14040
ggacaactat gatgaggcag acccagccac aattaggcct atagaggccg acccgtcagg    14100
ccgctcatac cacgtaggtc aagacccgtc tgctggtccc acattcacgt attataggag    14160
ttggtacgtg gcttacaact acggtgaccc acagactgga attcgcagca gtacgttgct    14220
ggtgacccct gacgttacgt gtggttcaga gcaagtatac tggagtgttc cggacatgta    14280
tgtagagcct gtgacgtttta aagctagcca aaacgtggca aattatcctg taattggggc    14340
agagctcatg cccgttcagt cgcgcagtta ttataacgcg caggctgtgt attcgcaaat    14400
gattcaagaa agcactaatc agacactggt ttttaaccgc tttcccgaca accagatttt    14460
ggtgcggccg cccgaatcta ctatcacgtt cgtcagtgaa aacgtgccag cgcagactga    14520
tcacggaacg ctccccatca gaaacagtgt gtctggggtg cagcgagtca ctctgactga    14580
cgctaggcgc agagccagtc cttacgtttta caaaagcata gccatagctc agccaaaggt    14640
tctgtccagc aggacgttct aaaatggcga ttttagtgtc cccaagcaac aacacagggt    14700
gggggattgg atgcaaaagc atgtatggcg gcgcccgcac gctatcagca aactttccag    14760
tgctcgtgcg aaagcactac agggccgtcg tggggaagca ggaaagggcg cgttgtcgca    14820
ccaacagttg aggttacaga cgaccctgtg gccgatgtag tcaacgccat tgctggtcag    14880
acacgccgcc gacgcggagc caggcgccgc aggcgcgcta cggcagcggt gcgcgccgct    14940
agagcgttgg tgcgaaatgc acggcgcacg ctagcccgta gggggcgcat gcggagaacc    15000
cggaatccag tggctgacgt ggtgagagca gtggaagcca tcgcacgcgc aaacccacgc    15060
cgtcgaagcg ctaggttgat ggcgcgtgct gccaacgcac cgcctccacg tccgcgcgcg    15120
aggaatatct attgggtgcg agacagtaat ggagtccgcg ttcctgtgac gtcccgccct    15180
ccaagaactg tggggactgt ggtttaataa agcctcgttt gctgcatcac acagcgcgtg    15240
cctgttcgtg ctttgtgcca acgtcaatgt cttcgcgaaa gataaaagaa gagatgcttg    15300
aaatcgtggc gccagagatc tatgcgccta gacgccggcg tagtgttaaa gttgagacaa    15360
aaacgaggat taaggtccca aaagatgaaa taaaatctaa acgcaagtgg aggcgtcctg    15420
gcatggctga catagatgag gtcgaaatac tgggagccac tgctcctagg cgcccgtatc    15480
agtggcgcgg taggcgcgta cagcgcatat tgcgtccagg aacggccgtg gtgtttacac    15540
```

```
cgggcgctcg tagtcgggaa cgagcaagca agcgttcttc cgacgaaatg tttgcggacg   15600
cagatatact ggaacagttt gaaagtggag atggcgagtt tagatacgga aagcgtggcc   15660
ggtctgaggc gctagtgttg gacgcctcta acccaactcc gagcatgcag cctgtaacgc   15720
cgcaggtacc tatcatgaca ccttcggtgg cagctaagcg cggcgctagc gcagtgccca   15780
cggtgcaagt actggcgcca agaagcgac gcatagacga gtagcgaca gacgatgtat    15840 ttgtcgctcc ttctccactt agcgagatgg acaccgtaga gccaggcacg gccgtccttc   15900
ttccttctag agcagttaag cgagttagga agagacgcgg agttgaagaa atcaagagcg   15960
atcctatggt tcttgaagaa gtaaaggtta gggatgtaaa accgatcgct cctgggatag   16020
gcgtgcagac aatagacgtg aaagtgccgg cggctcctcc agaataaag ccaccagtgt    16080 cagtggtgga gaagatggac ataagcacag ctcccgcgtc acgaatcacc tatgggcccg   16140
ccagcaagat atttccacag taccgacagc atccgagtca aatgggattt ccaaaagtag   16200
ttcgcactcg aaggcgcgcg gttaggagga gacgaaggcg ggcggcgccc attggtgttg   16260
aaattacagc cgcgcgaaga cgggcgctag gcgccgcata ttgcttccgc ctgttcgcta   16320
tcacccgtcc ctgcagacgg cgcctcgctc tcaggtcgca atctggcgtt gatcgatcat   16380
gcgaataaat tcctgtggta ctgcgtttag gcacctatct aacgcgatgg ctggcgtccc   16440
gagaatcacg taccgagtcc gcgtgcccgt gcacacacga gtgcggcgaa gtggaagact   16500
ggcgcggcgc gcgcctcgac gaaggggact taagggcggc tttctacccg ctctaatacc   16560
tatcatagcg gcggcaattg gcgctgcgcc cggcattgca tccgtagcaa tacaggccgc   16620
ccgccgcaaa taaagttagt tactgtctcc aagactcatt gttatcttta tttgcgccag   16680
ctgcctgcct gcgcccgtcg ccatggaagg aattaatttc tccgcgttgg ctcccagatg   16740
cgggtcaaga cccatgctta gcagttggtc tgatatcgga acaagctcca tgaacggcgg   16800
agcatttaac tggggaaacc tatggagcgg cgttaagtcg tttggcagct ccattaaaaa   16860
ctggggcaat cgcgcctgga acagtagcac tgggcaggcg ttgcgccaaa agctgaaaga   16920
cagcaacctg caggaaaagg tggtagaggg gttggctagt ggcattcacg gcgctgtaga   16980
tattgctaac caggagattg ctaaggcggt gcagaagcgc ttagagtcta ggccgaccgt   17040
tcaaatagag gatccagatt taatgtcaac agccgaagaa ctggatcgtg gaaaaaccgg   17100
ctccgtccac taaagcgcca gttaaagcca ctgtagaaga gtgtagcgaa aaaccgccc    17160 gtccgacgaa gaagagatag tcattcgtac agaggagccg cccagatacg aagacatttt   17220
ccccaataac tccgcggttc caataagcct gcgccctaca gcggttaggc cgtctgctcc   17280
agtagtcact gtaccggcgg cccgcccgt aaccacggaa attgtagaag ttcctccaac     17340
gagacctagc gctcgtccgg cggtggtgcc ttctagaaca acaagaggat ggcaggggac   17400
gctcaacagc atagtgggcc taggtgttcg atcagtaaaa cgaagacgct gtttttaagc   17460
atctcgctgc tctttccaag cgcgccccag tgatacccgg ccgcgaagat ggcgactcca   17520
tcgatgatgc cccagtggtc gtacatgcac atcgccgggc aggatgcctc agagtacctg   17580
tctcccggcc tggtgcagtt cgcgcaggcc acagagacct actttaagct gggtaacaag   17640
tttagaaacc ccactgtggc tccaacgcat gacgtcacca cagagcggtc acagcggctg   17700
cagctgcgat ttgttccagt tgaccgtgaa gacacgcagt acactcacaa gaccagattt   17760
cagttggctg tgggcgacaa ccgagtactt gacatggcga gcacttactt tgacatccgc   17820
ggtactttgg acagaggtcc aagctttaag ccatacagcg gcacggcata caacgctcta   17880
```

-continued

| | | | | | |
|---|---|---|---|---|---|
| gcccctaagg | ggtctatcaa | taacactttc | gtatccgtgg | ctggaaacaa | caacgccaaa | 17940 |
| gcttttgcgc | aagcccctca | gtcggcaaca | gtagacggaa | ctacgggcgc | catccaaata | 18000 |
| gacggcgccg | ccatcgacaa | cacctaccag | ccagaacctc | aaataggaga | ggaatcttgg | 18060 |
| ttgtccggca | ctgtgaaccc | aatcgcgcag | gctaccggaa | gaatactgaa | tacatctact | 18120 |
| gatcccctgc | catgttacgg | gtcttatgcc | gctcctacga | acattgaggg | agcccaaact | 18180 |
| cttaacaaca | atttgataca | agtgaatttt | gtggctggag | gcgcgcctgg | cgccccagac | 18240 |
| gtaggcatga | ttatggaaga | cgtggctctg | caaaccccag | acacacattt | agtgtacaag | 18300 |
| gtgccagccg | ccaacgtagg | caacacggcg | gccttagcgc | agcaagctgc | gccaaacaga | 18360 |
| gcaaactata | ttggcttcag | agacaatttc | atcggtctaa | tgtactacaa | cagcaatgga | 18420 |
| aacctagggg | ttttggcggg | gcaggcttcg | caattgaatg | ccgtcgtgga | cctgcaagac | 18480 |
| agaaatacag | agttgtctta | ccagcttatg | ctcgacaacc | tgtatgacag | aagccggtat | 18540 |
| tttagcattt | ggaaccaggc | tgtagacagc | tatgacccgg | atgttaggat | aatagagaac | 18600 |
| cacggagtgg | aagatgaatt | gccaaactac | tgcttcccaa | taagcggaat | agttcctggc | 18660 |
| accacctcta | ctagagtcac | cagaaacggt | ggaaactggg | aagccacggc | aaacaacgat | 18720 |
| ccggcgtatg | tcaacaaagg | caatttagac | tgtatgaaa | taaacctcgc | ggctaatctg | 18780 |
| tggcgcgggt | tcctatattc | taatgttgcc | ctgtacttgc | cagacgacct | taagttcaca | 18840 |
| ccgccaaatg | tcacacttcc | taacaacacc | aatacgtatg | catacatgaa | cggtcgcgtt | 18900 |
| ccagcggctg | ggttggttga | cacttacgtc | aacattggcc | ctcggtggtc | gttggatgtg | 18960 |
| atggataacg | tgaacccatt | caaccatcac | agaaacgcgg | gcctgcgcta | ccgctctcaa | 19020 |
| cttctaggca | atgccggta | ctgtcatttt | cacatccaag | ttccgcagaa | gttttcgcc | 19080 |
| atcaagaacc | ttcttctgct | gcctgggacg | tacacttacg | aatggtcttt | cagaaaagac | 19140 |
| gttaacatgt | tccttcagag | cactcttggg | aatgatctgc | gtgtggacgg | agcctccatc | 19200 |
| acaattgaga | gcgttaacct | gtatgccagc | ttttccccaa | tggcacacaa | taccgcatcc | 19260 |
| actcttgaag | ccatgctgcg | caatgacaca | aacgaccaat | cgttcatcga | ctacctgtct | 19320 |
| tcagccaaca | tgttgtatcc | aattcctgcc | aatgccacta | acctgccaat | tccatccca | 19380 |
| tctcgcaact | gggccgcctt | ccgcggatgg | agcttcacca | gaattaagca | gaaagaaaca | 19440 |
| cccgccttgg | gctctccatt | cgaccccctac | ttcacatact | caggcactat | accatacttg | 19500 |
| gacggcacct | tttatctcaa | tcacaccttc | agaagggtgt | ctatacagtt | tgattcgtcg | 19560 |
| gtgcagtggc | cgggcaacga | ccgcttgctc | acaccaaatg | agtttgagat | taaaaggcta | 19620 |
| gtggatggag | agggggtacaa | tgtagctcag | agcaacatga | caaaggactg | gtttctagtg | 19680 |
| cagatgcttg | caaattacaa | cattggctac | cagggctatc | atctcccgga | tggctataaa | 19740 |
| gatcgcacat | attcttttct | gagaaacttt | cagccaatga | ctaggcagat | agtggaccaa | 19800 |
| actaacgtgc | ccgcgtatca | gaatgtccca | atcacccacc | agcacaataa | ttctggctttt | 19860 |
| actggatttg | ccagtccagc | gctgccgcgt | gagggacacc | cgtatccagc | taactggccg | 19920 |
| tatccactga | ttagcgctac | tgcagtggcc | acgcaaacac | agcgaaagtt | cctatgtgac | 19980 |
| aggacgctgt | ggcgcattcc | attctcgtcc | aactttatgt | ctatgggatc | gcttaccgat | 20040 |
| ctggggcaga | acctgctgta | tgcaaatgct | gctcacgcct | tagacatgac | ctttgaagtg | 20100 |
| gacgcgatgg | acgagcccac | gctgcttat | gttttatttg | aagtgtttga | cgtggttcgc | 20160 |
| gttcaccagc | ctcacagggg | agtcatcgaa | actgtctacc | tcagaactcc | attctctgcc | 20220 |
| ggcaacgcca | ctacataagc | atgggatcca | gggaagagga | actgcgcgcc | attgtgcgcg | 20280 |

```
acctcggagt tgggccatac ttcctgggga cgttcgacaa acgctttcct ggttttctaa   20340
ataactcaaa gccgagctgc gccatcgtga ataccgcagg tagagaaaca ggcggcgcgc   20400
attggctggc cctggcttgg ttccctaaat ctaaggcttt ttacttttt gatccatttg    20460
gattcagtga tagcaaactg aagcagatat atgagtttga gtatgaaggt ctgctgcgcc   20520
gcagcgcctt ggcggctact ggcgatggct gcataaacct ggttaagagc agtgaatcgg   20580
tacagggtcc gaacagcgcc gcctgtggct tattttgctg catgttttta catgcttttg   20640
ctcactggcc ccacagtcct atgacccaca accccaccat ggacttgttg actggtgtgc   20700
ctaaccataa cattatgtca cctagcgccc agcccacact gcgagaaaat caagtcaagc   20760
tttataagtt tctagcagcc cattctcagt actttcgcac ccatcgcccc caaattgaac   20820
gagacacctc ttttaataaa ctgctggaat caaaattgca ataaatgatt ttattttgaa   20880
tcaacatttg agcagcgtgg tgtgttcaaa ataacgcgtc gtcggcgtct tcctgaccgg   20940
tgggtaggat ggtgttctgc actctgtact ggggaagcca cttaaattct tgcacgacaa   21000
tgggcggttt cgtgccaacc attgaattcc agatttgctt tgcgagctgc agccccatga   21060
ctacatctgt cgagctgatc ttaaagtcgc aattcttctg agggtttgct tggtattgc    21120
gaaatacagg gttgcagcac tgaaatacaa gcactgcagg gtggtctagg gtggccaaca   21180
ccttagcgtc gtcaatcaag gcgcgatcta tgctgttgag tgcagtcatc gcgaacggcg   21240
tgaccttgca cgtctgcttt ccaagcaggg gtagaggctg atgaccgtag ttacaatcac   21300
ataccagcgg cattaagagc atctcaccag cttttggcat gttgggatac atcgccttta   21360
caaaagcgcc tatctgcttg aaggccatca gcgccttggg gccatctgtg taaaaatacc   21420
cacaagactg agagctaaaa ctgttgattg gagactttag atcatgatag caactcatcg   21480
cgtcgctatt cttgacttga accacgctgc ggccccagcg gttggtgaca atcttcgcgc   21540
gctcaggtgt atccttcaat gctcgctggc cattttcgct gttaatgtcc atctcaatga   21600
tctgctcctt gtttatcatg ggcaagccgt gcaaacaata caatttgtcc tcgtctgcct   21660
tgtgctccca cacaacacaa ccagatgggt tccaatctgc cgccgttata tcggcgccgc   21720
gcagaatgaa atccagcaaa aaacgcgcta tcaccgtctg caggctcttc tgagtagaaa   21780
acgtgagttg gatgaatttt tttcgatcat tcatccacgc ctgggctgct tttttcaggc   21840
actccatggt gccggaatca ggaagcaagg taaggtcttt tatgtccact ttcagtggca   21900
cgagaataga cacagccaaa tccattgcgc gttgccactt ctgctcattt ttgtcaatca   21960
actgacgccc catacgagcg acctgggata gctgcgggtc ttggttcttc ttgcgtccct   22020
ggggcgatct agaagggcct ggctgctcat cgtcggtgtc ggaaattggt ttcgattttt   22080
tacgctgcgg gccatccagt aacgcttcgg cgctctgcgg cgcagcgtcc tcactgacgg   22140
ctttgcggcg tctggcaacg cgctttggct tcggtgtttc gtcaatgaac agcttgccct   22200
cgtcgccgct gctttcagac acatcctcat agtgataccg gctcattttc cttctagatg   22260
gaagaacaca gcgtcagtc cagctccgag ccggcgccga atcacgagcc gcggagctt     22320
agcttagaag atgctttgtc tccccaaccc gcggttgaaa gcgccgctcc gggttccgag   22380
gatgaaagcg aagctctcaa acactacatt gactccgacg tgctatttaa gcacatcgct   22440
agacagagtc gcatcctcaa agatagcctc gccgaccgct ttgaagtgcc tacagacgcg   22500
ctagaactaa gtctagcgta tgagcgctct ctatttctc catctacccc acccaagaag    22560
caagaaaacg gcacctgcga gccaaaccct cgaatcaatt tctacccaac cttcatgctg   22620
```

-continued

| | | | |
|---|---|---|---|
| ccagaaacac | tggcaacata | tcacatattc | ttttttaacc acaaaattcc gctgtcgtgt | 22680 |
| cgcgctaatc | gcagtcgagc | cgatgaaaag | ttaatgctaa cagaaggaga ctgcatacct | 22740 |
| gattttccaa | ccacggatcg | ggttccaaaa | atcttcgaag gtttgggctc agaagagaca | 22800 |
| gtggcctcca | actcactaga | agagaaaaga | gacagcgctt tagtagaact gcttaacgac | 22860 |
| tcgccgcggc | tcgcgattat | aaagcgctcc | acagcgctga ctcatttcgc atatcccgcc | 22920 |
| ataaacatgc | cgccaaaagt | gatgagttgt | gtcatggagg aaatgattgt gaaaaggcc | 22980 |
| gaacccgtgg | gagaagagtc | gacacctgac | ggtccagaag ggggcgcgcc agttgtcagt | 23040 |
| gacgcagaat | tggccaagtg | gcttggaagt | agcgacgcca ccctgctcga agacaggcga | 23100 |
| aaactgatga | tggccgttgt | tctagtaaca | gctcagctgg agtgcatgaa aaggttttt | 23160 |
| acttcttctg | acatgatcag | aaagctaggt | gaaacgctac actacacttt caggcacgga | 23220 |
| tacgtcaaac | aagcctgtaa | aatatcaaat | gtcgaactac caaacctggt atcatacatg | 23280 |
| ggcatacttc | atgaaaacag | actaggtcag | cacgtactgc acaacacact ccgcgatgaa | 23340 |
| cagaggcggg | actacattag | agacaccatc | tttctgatgc ttttgtacac atggcagaca | 23400 |
| gcgatgggag | tgtggcaaca | atgtcttgag | gtcgaaaaca tcaaagaact aagtaaactg | 23460 |
| ctcagacgaa | agagacgggc | gctttggaca | ggctttgatg agcgaacaac cgccggcgac | 23520 |
| ctagccgaca | taatctttcc | gtcaaaactg | ctatcgacat gcaagccgg gctaccggat | 23580 |
| tttacaagcc | agagcatgat | gcaaaatttc | cgcagcttca tattagaaag gtctggaata | 23640 |
| ttgccagcat | tatgcaacgc | catacsttca | gactttgtgc caatagaata caaagagtgc | 23700 |
| ccgcctccgc | tatgggcata | ctgttatttg | ctaaaattgg caaactacct aatgttccac | 23760 |
| tctgacgtag | cttttaatat | ggaaggagag | gggctatttg agtgctactg tcgctgtaac | 23820 |
| ttgtgcaccc | ctcaccgctg | tcttgcaacc | aacactgcct tactaaacga ggtgcaggcc | 23880 |
| attggcagtt | ttgagcttca | aaggccccca | atcctgacg ggtctatgcc tcccacactg | 23940 |
| aaattaacgg | cgggggcttg | gacctcggca | tatttgagaa atttgaacc tgcagactac | 24000 |
| cgtcacgatc | aaattcgatt | ctatgaggac | caatcaaaac caccaaaatc cgagccatct | 24060 |
| gcctgcatca | tcacgcaagc | cgccattctc | gcccaattac atgacataaa aaaagagcgg | 24120 |
| gaaaaattct | tgcttaaaaa | gggccacggc | gtgtacctag accccaaaac aggcgaagag | 24180 |
| ctcaacacgc | tagagccatc | agtctctcac | aatgccgcga ccgtcagac cgaccagtct | 24240 |
| aaatttgaca | aaaccgaagt | cgcggaaaaa | agccgcgcca gaaccccctc ctccaacgcc | 24300 |
| agacgaggaa | actctggaga | gcattccagg | cgaggacgta gaggaggaat gggacgatat | 24360 |
| agacagtttg | gtcgcggagg | agagcgagat | ggaggacgag gaattggagg atggcgagac | 24420 |
| atcagtctcg | gagctattaa | agaaggatca | gcctccgccg ctcccgccga aaacaaggaa | 24480 |
| ggccccaaaa | cagcgtagat | gggaccaaac | tccaacatcg gcccctggta agcagaactc | 24540 |
| gtcggtggga | ggaaaataca | agtcgtggcg | tccccacaaa catcacataa ttacggctct | 24600 |
| gctggcaagc | gggtatgacg | tgtccttcgc | ccgcagattt atgctttacc gccacggaat | 24660 |
| aaacgttcca | aaaaatgtaa | tccattacta | caattcccaa tgcaggacag aatccccaga | 24720 |
| agaagtctgg | aaagcgaaca | atccagtcag | ccagtacatc cgcagagccg gcgacgaccc | 24780 |
| aagagctgag | agctaaaata | ttcccaacgt | tgtacgccat attccagcaa agcagaggtg | 24840 |
| gcggagtatc | tctaaagata | agaaccgat | ccttaagatc cctcacaaaa agctgccttt | 24900 |
| accacaagca | ggagagtcag | ctgcagagaa | ccttggaaga gcgccgaggct ctactccaga | 24960 |
| agtactgttc | cgggctgaga | ggctctgcgc | cttatatctc agctcagcat gagtaaagac | 25020 |

-continued

```
atccccaccc cttacgtatg gactttccag ccccaattgg ggcaggctgc cggcgcgtca    25080
caagactatt cgactcgcat gaactggcta agtgcaggtc cttcaatgat taaccaggtg    25140
aactctgtcc gagccgaccg aaacagaatc ttattgcgtc aagctgcagt atcggaaacg    25200
cccagactcg tccgcaaccc gccaacgtgg cctgcccaat acctatttca gccaattggc    25260
gcgcctcaga cctttgagct tcccaggaat gagtcattgg aggtggcaat gagtaactcg    25320
ggcatgcaat tagccggggg cgggacgcat cgcactaagg atataaaacc agaagacata    25380
gtgggacgcg gcctagagct gaacagcgac attccgagcg cttcgttttt gcgtcctgac    25440
ggagttttcc agcttgccgg aggtagccgt tcctctttca acccaggact gagtaccttg    25500
ctcacggtac aacctgcttc aagcctgcct aggtccggag gaatcggcga agtgcaattt    25560
gtgcacgagt ttgtgccgtc cgtgtacttt cagccttttt caggaccacc tggaacatat    25620
ccagacgaat ttatctacaa ctacgacata gtctcagatt ccgtcgacgg ttatgactga    25680
tacagagtct gatctttcgc tgtttggtgt ctgccggctg cactactccc gctgccagtc    25740
taccaactgc ttctggaagc agggaattct gccaacctac cagtgcattt tagacgcgga    25800
cctccacgcc gactgcgtgc cagactccct gcaagccggc cacagcctgc ggctcgaact    25860
gccacaccgt tttgcctgtt atcaaacctc aaatacggga ttgcctatcg tgtgctccag    25920
caatgtcaag tcaagcagct tcaaagttac atgctcctgt tccagtactg ggatgcatct    25980
ggcgctcgcc gatgctctct gtgatcttgt taaccattct atggcagatg aagagcgcta    26040
aatcgctgcc gcacaaccac acagcggtaa tccccaggag tgtctgcgtg ccaacgtttt    26100
cctgtacagg tgtggtgagt gcgacggcga ccctcacaga cgcccagact accgcatcag    26160
ccgcgcgcca ccagtgggta tgcgtagtat ccatcaactc cagcagcgac acaacgtgtg    26220 tttgaacgg ttggacatac aaagaatttc cgcttgaaat tcaattggac gaacgcttag     26280
ccgacacccc tgtggactgt gtggaaggaa ggcgccgcac aacatttgac ctaagagctc    26340
tgtgtcggtt tcgctacacg cctctatatg ttttgaaatt agccataccca atctatgcga    26400 ctgtgcttac cattgtgggg gcgctcattg cgtttccggc tctgcgctcc cctctcgcca    26460
tcagcatgct cccagcagcc atggcagata atggctacca ccaccaccac acctgcgcgc    26520
cgttgctact gaccatatta atgttaatcg ccatgctgtg taaggtcacg aagcccacaa    26580
acaaactttt catcttagct cttcttagtc tagctgtgcc aggaaattgt ttgaaccagt    26640
acagtgtgct agaagggagt ccatgtgaac ttaaatctgc aacaaaacgc tacaccaaag    26700
cctcatggta tcgcgactct gaatctgcgc tgctttctcc tttcgccaca atcagtcaat    26760
cctcagtaac atactcttcc ccatcctcca gaataatcct agcttcaaac ttgtctctaa    26820 ttttacttc tgtaaaacct tcagacaacg gatcctattt tctaagcatc gactatcgcg     26880
aatttatcaa gtatgacctg cttgttagtc ctaaaattca aatcaaccta gccatacaaa    26940
cacagccagg agttaatcac acatgcataa tttctgccac ttgcagccca cacagcgccc    27000
agtacaggtc agtgatcaag tggcagaacc acacttacca ttcaaaagcg cttttcacag    27060
ttttcactga gcagttaaat aacaacataa catgcacagt gtcttctcct cttgaaacta    27120
attccaagtc tttaacagcg tcacaaatgt gtgttttca caatcctaat gacttcagcc     27180
ctctaatcat tgtaggtgtt ttaactcttg tgttcatagc catatggatc atctctatgt    27240
ttcatactgt acgcgtccca atctttaagt atgaactggt gatataaatc aataaactca    27300
cgtgattatt agacgcagct tctccgggtc ttcttttccc caacaatcta ttacagctcc    27360
```

-continued

```
ttcgtcaaga ctgacataac gcaacttaag caggtaagct aactttctaa attgcctaaa    27420
aggcagcaaa acactaccta acggcactcc attatacttt atctccattg cagttatccg    27480
caatgaagcg ctcgattccg tcagatttcg atccagtata tccctatgga aaaagacctt    27540
cacttaatat catgccgcca ttttacagcc aagacggttt tcaagaagca ccaaccgcca    27600
ccctctcact caaaatcaca gacccaataa cgtttaattc cagcgggca ctttcagtta     27660 aagtgggagg gggaataact attaaccaaa acggccaatt agaaactact aacgcgacca    27720
cagcagttaa cccaccatta gagtatgcta atggggcgat aagcctaaat accggaaacg    27780
gactggcagt tgactcaact caaaatctga caattcttac atcgagccca cttgccgtgt    27840
cacaatctgg tttaacgctg aacacaggtg atggcctaga ggtggatggt gatgaagtga    27900
aagttaagag cgggcaaggt gtgagtgtag gcactactgg agttgggata atgccgcct     27960 catactttgc ctttccctca aatgtattat ccctccttac tacagctcct ttaagtgtat    28020
ccagcggctc tcttggagta gagctaggca acggattaca agtgtcaaat gaccaactga    28080
cgctcaacac acagccacta tttacatttt ccaacggggc aatggggctg gcagtcggca    28140
acggaatcca aatagaaaat aacgctgtcg ccatttatgc ccaaccatat ttccaataca    28200
ccaacagagc cctgggcctt cgccttggaa atggcctgca gaccgaaaat aatgcaattg    28260
ccttatattg tcagccgtac ttccaatata cagataacgc actagcgctg cggctagggc    28320
aaggactgca aatctccaac aatcaagtag ctttatatgc tcagtcttac tttcaatata    28380
ccaataatgc attggcattg cgcttagcga acggtttagg cacgtctaac aataacgttg    28440
ttgtaaatta tggaaaaggc ttatttataa actcaagcga ttcaaacaaa ttgcaagtga    28500
atattagatc tccgctaaac tactatggca gttcacacac aattggtcta aatacaggaa    28560
acggtctaac tgttactagt cttggcgcgc taggtggcaa tgtatccgtt aatattggaa    28620
gcgggctatc ttttagctca actgggcagg tgcaggcttc attaggaaac gggctccaaa    28680
tcgcttccag tgccatagaa gtcaaactag caacggtttt acagtttgac aatggcgcca    28740
tttccctatc agggtcatct cccgcctaca cagactacac tttatggact actccggacc    28800
cctctccaaa cgctaccatc agcgcagaat tagatgccaa gctggtgctt agtatttcaa    28860
aagcaggaag cactgctatc ggcaccatcg gtgtagttgg attgaaaggg cctctattaa    28920
gtttggccga gcaagccatc aatgttgaaa tttactttga caccagcggt aatattattt    28980
ttagcacaag cacgctgaag tcatactggg gatttaggtc tggtgattca tatgatccaa    29040
actccacact taatcctctt tatttaatgc caaatcagac cgcatacct ccagggcgac     29100 aaaccataac ccaaatagcc tcacttgaag tgtacttagg tggggatact accaaacctg    29160
ttcttttaga ggtagctttt aacaccgcaa gtagtggcta ctccctgaag tttacttggc    29220
gaaacttggc cagctatgcc ggacagacct tcgctgtatc ccttggaacc ttcacatata    29280
tcacacaaca ataaataagt tttaacatct ttatttgagt cgtgaatttt gtggcatcac    29340
tcttacagtc attccaccac caccactcca tgcaacctta tacacaagcc tttcaaaatg    29400
cattccagtg ttataacaat cagctttttt atgcaatttt acagcatgtt cataacattc    29460
aaagtcaggg gaagttatag agacaaagcc agcgggcata gactccaaag atggtttcag    29520
gtctaaaagt ttggatgcgt gtccacagtg tggtgaggct gattctccgg aggttctttc    29580
tggagcagat agcacttggg gcagccgcag cggtacttcg tcatcctcac tttgcagatc    29640
ggagtccctc tcgcaatcgc tagagtctcc actccaggaa caagacgaag ttccagactc    29700
ggtgtcgctg actcgtccca gatctgacat tctgaagcct caagtccttc tagtccacac    29760
```

```
aagtcggaca aagaacacct ggcataccac ccaaacggaa catcgatcga cacattaaac    29820
ttcattactc tagaactgcc cgcagttaat aacatatcac tttccgcaca caaatgagcc    29880
gtttccccac ttctaatagg ggccgggtta tgtgagcgaa aaagacagcg aggaattcgc    29940
cgcctacctt cccattcttt cctttcgctt tcgctcatcc tagcccatcg ccgctcaaat    30000
cttaatttat tccttggctc gcaagcgtca tgcccacaat catcatattc acaatcagca    30060
tatttataca tcaagacagg cgtgccggcg cgcaaagcga tagggccttc ttcttccccc    30120
caccaaggca gctctatggt aaatcctgga gaggtgcata gtgacaaatg actgctaaat    30180
gcccaagaaa acactttag atctggatta aacaatgatg aaagcatccc aactccataa    30240
tagccgtccg gatttctaat ctttacatca aacactatta cagttttttc ttttgtgaga    30300
attacatctt cttcaagaca cagatgaacc accgtcttgt cgctgttaaa gattggccgg    30360
tgtttgcatt tctccccaac ctcgatatta attggaggcg tgctcattct gaaagagatt    30420 tttttttcaat tgaaattttt actactggct ctccaggatt agcataaatc acatagtcta    30480
cccactcata cattttacac actatatttt taatcaaatt tggctcatgg gtgatgtctg    30540
catacagcca tggaactaaa catgaaacac tgaaatcata accgggggt ataaacactt    30600 catgatctaa gcagaagtcg ctctccccat atggcaggaa aaccatttt ttaggtgcca    30660 gcagccacac ttcattatcc gacttaagta tcggagcaag tgcatctgga ccggtgtaga    30720
caaataactt caactgcatc tgcaacacaa atgcgattta cgcgtcaagc gcttaatcaa    30780
gcgttgcttg ttgcgctcat actcgctagg tggcagtgaa agaatgttac atgcactgcc    30840
agcaagcagt aacaccgttc tagttctctc tgcacatgct aatgcggcca cctgtgtcat    30900
ttcatgacag tgtctacaaa ttattacaag atacaccccg gtataaccta tgcaaaacac    30960
cgccccttca aacctaagat tacgaattcg tggcacatcg ccccagtaat taatctttat    31020
aaaaatcaaa tgcaaacccc taaacataat actaccctca tataacagcc taaagcttaa    31080
atctttgtta gtcagtggcc tataaaatgg aaacctaata ttgtattctg tcccaccac    31140 cagctctttc acaatgtcag taataaagcg cctgcgtgac aaggcttcca aagtgctccc    31200
ttcatgcaaa tcatgacaac aaacagacca tttaaagcct ttattccttt tgaacattaa    31260
ttcaatgtct ccaccacatt caacttttaa gcgagtcccc aagcacagat aatctttcaa    31320
caatctatat tgccaagaaa caagaatact tttccatgga attggaattt ctaaattcat    31380
agccaatggc agagctgact gtggagaatc aacataagaa ataattttgt gctgaaattt    31440
cgaccgagtg gactccgctg tcatctgtaa ttaaagatat ttaacatatt tttgagacat    31500
tggcaggcca tacttcataa gctgcaacag ctctctctgc ctaactacct cttttttgct    31560
tggctgttta gggccagagc agcaacccac agctcttttt aataggcgcc tagttcgttt    31620
tgcacacacc ttggcttgaa tttcagataa attacatgac ctgcaaataa ctattaaaaa    31680
atttccatac aaaccatcca catatacagc ctctccaaaa tttaatttac gaattctctt    31740
catgtcgcca tctaaaatta ctctgatgta tataaggtgg atcccacgaa tgtaaacact    31800
acccatgtac atcaacccct ctggtaaatt cttattcaca cacccctgt aaaaccaaaa    31860 tagctgattg taaaatgtcc cttttaaaac ctcttgaaac agtccagtaa gcactttacg    31920
ggaagacaag cactgaagac tgccagagtt gtcacaatgg caatgtaaat accatcttga    31980
ttgcaatgaa gaaaaatcag gttgaagatc tttagagaac acagaacaca tctctagttc    32040
aacgccgtca cacaaatggc gcttcaaaaa cacaaactca tgatgactta atatatgcat    32100
```

-continued

```
ccatggcacc ggcagttcca agcacatagc aaaacaggca gcagtgcgcg gtgagcgaac    32160
aaaggctact ggatgactgt ctgttgaatt gcaacaaatt aggccgctgc ctggaacctc    32220
aaaatgctcc atcctcaatc ttaagcagaa gctgtcgcag tttaggttcg acggaactcc    32280
aggagcagaa agcctcagca acctcttcgg gcactccctc gcccctaggg ccgcaattga    32340
tgtaattggc caacacaaaa ccaacgtagt gcacttggcg cattagagtc tggtctgctt    32400
tcctggtgaa atgaattttc gcagttgact gattggaaga gtaaataatt gagattatct    32460
ctgatgattt ctgcaacgca agcgcctcag ttgaaatgct cattgggtaa taatcacgaa    32520
gaatgcgctt cttaaagtga agacgtctgg atgtcattac tgcaataatg caacagtgat    32580
tgttttacat tcttccagac tcacatcctc accgattaat ctaaggtaat catacaaagc    32640
ctcatgtagg taatcccgca aatccgaaac taagaagtct tcatcactgc ctccattagt    32700
cagcaaagcg tccatagagc ttccagcaag gcaaaataat caacatagtt gcctcaagat    32760
ccgtatgatg ataggagcta acgtacagca agttagaacc agagaaatat aaagaagctc    32820
tggcagtcac aaaagccttt gccatagatg aaacagaagc aatgaaagat tctctattct    32880
ccacctgaag gcgagatgta aggcaatggg gaatggaaat ctgcatcatc tccccgtctc    32940
taacaggtgg tgccattata ctccagtaga tccaaatccg ccttcccctc gctcagtgtc    33000
gtcaagtgta tcaacctcct gaacctcagg caatgagatc ttttggatga caagctgagc    33060
tacgcgctgg cctggcgaaa taaggacgtg atgattccca tggttaaaga gcaggacgaa    33120
cacctctccc ctgtagtcgc tgtcaatcac gccagcgccc acatccaagc cttgagtcac    33180
agacaagcca gagcgaggtg caacgcgtcc gtagtgtccc tcaggaatac ggagctttag    33240
gccagtaggc acaagagcgc gagatccagc ctgaatctca acgtaatgcg aagcgcacaa    33300
atcatatcca gccgcaccat tagaagctct tttaggaggc acagccgagt cagacacacg    33360
cacaaagagc agcttgtcag ccatgatgta cttactcttg gcaaagtaga ccacggccta    33420
cagcaaggag tgtaagttta gaaatggcag cacagaaggc tcaggagcag aggcgaatga    33480
cgagcagagg agagaaatgg ctttatagag cgaaaaggcg cggtctgtga cgaggcgaaa    33540
gggcttctgg cgcctgacag gcgtaaccga aaccgcgtga caaagcacaa gacagtgcaa    33600
aagggcagtg actcagcgcc tcgccccgcc gctcgcacgc acacggacac tccccgcccc    33660
tcccagaaac tcccgcccag cgacctttga acaattttcc cacgccccct tacgcacagc    33720
acgtcaacgt catcacgcaa aagtgttccg tatattattg atgatgtcaa gagtggcacc    33780
tctttacctg cgcaggtaat atatagctca ctgggagtgg tgcatagaga aaaaagaccg    33840
cccatgatgg gagacgtggc atagaccttt agacaggttt cgtgcggcat cgcagtaaaa    33900
gtggccataa attgggaaaa atccctccac gtccgcgggc aaagggctcc aataaagtgg    33960
caaatttacg acagtgaaag tcaaagtcca acagctgata ccctaaacac cccatcataa    34020
atacacctga ctcagcgcct cgccccgccg ctcgcacgca cacggacact ccccgccccct   34080 cccagaaact cccgcccagc gacctttgaa caattttccc acgccccctt acgcacagca    34140
cgtcaacgtc atcacgcaaa agtgttccgt atattattga tgatg                    34185
```

<210> SEQ ID NO 4
<211> LENGTH: 6
<212> TYPE: DNA
<213> ORGANISM: Artificial Sequence
<220> FEATURE:
<223> OTHER INFORMATION: Description of Artificial Sequence: Synthetic DNA Linker -continued

```
<400> SEQUENCE: 4 ctgcag                                                                    6

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: DNA Primer

<400> SEQUENCE: 5
ggccttaatt aacatcatca ataatatacg gaacac                                  36

<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence: DNA Primer

<400> SEQUENCE: 6
ggaagatctt gagcatgcag agcaattcac gccgggtat                               39

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: DNA Primer

<400> SEQUENCE: 7
ggcaatgaga tcttttggat gacaagctga gctacgcg                                38

<210> SEQ ID NO 8
<211> LENGTH: 41
<212> TYPE: DNA
<213> ORGANISM: Artificial Sequence
<220> FEATURE:
<223> OTHER INFORMATION: Description of Artificial Sequence: Synthetic DNA
      Linker

<400> SEQUENCE: 8
ctgtagatct gcggccgcgt ttaaacgtcg acaagcttcc c                            41

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA Linker

<400> SEQUENCE: 9
aattcgagct cgcccgggcg agctcga                                            27

<210> SEQ ID NO 10
<211> LENGTH: 42
<212> TYPE: DNA
<213> ORGANISM: Artificial Sequence
<220> FEATURE:
<223> OTHER INFORMATION: Description of Artificial Sequence: Synthetic
      DNA Linker

<400> SEQUENCE: 10
gactctaggg gcggggagtt taaacgcggc cgcagatcta gc                           42
```

```
<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: Synthetic
      SmaI Site

<400> SEQUENCE: 11
gaattcgagc tcgcccgggc gagctcgaat tc                              32

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA Linker

<400> SEQUENCE: 12
ctgtagatct gcggccgcgt ttaaacg                                    27

<210> SEQ ID NO 13
<211> LENGTH: 14
<212> TYPE: DNA
<213> ORGANISM: Artificial Sequence
<220> FEATURE:
<223> OTHER INFORMATION: Description of Artificial Sequence: Synthetic
      DNA Linker

<400> SEQUENCE: 13
tcgacaagct tccc                                                  14

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA Linker

<400> SEQUENCE: 14
cccgggagtt taaacgcggc cgcagatcta gct                             33

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Synthetic
      DNA Linker

<400> SEQUENCE: 15
gaattcgagc tcgcccgggc gagctcgaat tc                              32

<210> SEQ ID NO 16
<211> LENGTH: 14
<212> TYPE: DNA
<213> ORGANISM: Artificial Sequence
<220> FEATURE:
<223> OTHER INFORMATION: Description of Artificial Sequence: Synthetic
      DNA Linker

<400> SEQUENCE: 16
tcgacaagct tccc                                                  14
```

```
<210> SEQ ID NO 17
<211> LENGTH: 10
<212> TYPE: DNA
<213> ORGANISM: Artificial Sequence
<220> FEATURE:
<223> OTHER INFORMATION: Description of Artificial Sequence: Synthetic
      DNA Linker

<400> SEQUENCE: 17
caagcttccc                                                                    10
```